United States Patent
Chakrapani et al.

(10) Patent No.: US 9,393,295 B2
(45) Date of Patent: Jul. 19, 2016

(54) NANOPARTICLES FOR USE IN PHARMACEUTICAL COMPOSITIONS

(75) Inventors: Aravind Chakrapani, Bangalore (IN); Manmohan Singh, Lexington, MA (US); Derek O'Hagan, Winchester, MA (US)

(73) Assignee: Novartis AG, Basel (CH)

(*) Notice: Subject to any disclaimer, the term of this patent is extended or adjusted under 35 U.S.C. 154(b) by 408 days.

(21) Appl. No.: 12/990,110

(22) PCT Filed: Apr. 28, 2009

(86) PCT No.: PCT/US2009/041932
§ 371 (c)(1),
(2), (4) Date: Oct. 28, 2010

(87) PCT Pub. No.: WO2009/134769
PCT Pub. Date: Nov. 5, 2009

(65) Prior Publication Data
US 2011/0038900 A1    Feb. 17, 2011

Related U.S. Application Data

(60) Provisional application No. 61/048,428, filed on Apr. 28, 2008.

(51) Int. Cl.
*A61K 39/095* (2006.01)
*C08J 3/14* (2006.01)
*A61K 39/00* (2006.01)

(52) U.S. Cl.
CPC ............... *A61K 39/095* (2013.01); *C08J 3/14* (2013.01); *A61K 2039/55555* (2013.01); *A61K 2039/62* (2013.01); *C08J 2300/16* (2013.01); *C08J 2367/04* (2013.01)

(58) Field of Classification Search
CPC ........ A61K 39/0395; A61K 39/00; C08J 3/14
See application file for complete search history.

(56) References Cited

U.S. PATENT DOCUMENTS 5,049,322 A    9/1991  Devissaguet et al.
5,118,528 A    6/1992  Fessi et al.
(Continued)

FOREIGN PATENT DOCUMENTS

EP    0274961 A1    7/1998
JP    63088033 A    4/1998
(Continued)

OTHER PUBLICATIONS

Niemetz et al, Biosynthesis of the dimeric ellagitannin, cornusiin E, in Tellima grandiflora, 2003, Phytochemistry, 64, 109-114.*
(Continued)

*Primary Examiner* — Trevor Love
(74) *Attorney, Agent, or Firm* — Helen Lee; Virginia Campen

(57) ABSTRACT

In various aspects of the present invention, nanoparticle compositions are provided which comprise (a) nanoparticles comprising at least one biodegradable polymer and (b) at least one pharmaceutical associated with the nanoparticles. In other aspects of the present invention, methods of forming nanoparticles compositions are provided, which comprise contacting a first liquid that comprises one or more biodegradable polymers dissolved in a first solvent with a second liquid that comprises a second solvent which is miscible with the first solvent while being a non-solvent for the one or more biodegradable polymers, such that nanoparticles are formed.

49 Claims, 1 Drawing Sheet

(56) References Cited

U.S. PATENT DOCUMENTS

| | | |
|---|---|---|
| 5,133,908 A | 7/1992 | Stainmesse et al. |
| 6,884,435 B1 | 4/2005 | O'Hagan et al. |
| 2002/0136776 A1 | 9/2002 | Fang et al. |
| 2009/0061010 A1* | 3/2009 | Zale et al. .................. 424/501 |

FOREIGN PATENT DOCUMENTS

| | | |
|---|---|---|
| WO | 96/20698 A2 | 7/1996 |
| WO | 9702810 A3 | 1/1997 |
| WO | WO-97/03657 A1 | 2/1997 |
| WO | 00/06123 A1 | 2/2000 |
| WO | 02/26209 A2 | 4/2002 |
| WO | 2004/065578 A2 | 8/2004 |
| WO | WO2004/065578 * | 8/2004 |
| WO | WO-2007/100699 A2 | 9/2007 |
| WO | 2008/051245 A2 | 5/2008 |

OTHER PUBLICATIONS

Jackson et al, Effect of agitation of BACTEC 13A blood cultures on recovery of *Mycobacterium avium* complex, 1991, Journal of Clinical Microbiology, 29(9):1801, pp. 1801-1803 and title page. (4 pages total).*

Shuvaev et al, Factors modulating the delivery and effect of enzymatic cargo conjugated with antibodies targeted to the pulmonary endothelium, 2007, J Control Release, 118(2), p. 235-244.*

A. Pashine et al. Targeting the innate immune response with improved vaccine adjuvants, Nature Medicine Supplement, 11(4), Apr. 2005, S63-S68.

K. S. Rosenthal et al., Vaccines: All Things Considered, Clinical and Vaccine Immunology, Aug. 2006, pp. 821-829.

J. Wendorf et al., A Practical Approach to the use of Nanoparticles for Vaccine Delivery, Journal of Pharmaceutical Sciences, 95(12), 2006, 12 pp.

U. Bilati et al., Development of a nanoprecipitation method intended for the entrapment of hydrophilic drugs into nanoparticles, European Journal of Pharmaceutical Sciences, 24 (2005) 67-75.

D.T. Birnbaum et al., Optimization of preparation techniques for poly(lactic acid-co-glycolic acid) nanoparticles, Journal of Nanoparticle Research 2 (2000) 173-181.

H. Fessi et al., Nanocapsule formation by interfacial polymer deposition following solvent displacement, International Journal of Pharmaceutics 55(1), 1989, R1-R4.

Ruxandra Gref et al., "Biodegradable Long-Circulating Polymeric Nanospheres," Science, Mar. 18, 1994, vol. 263, No. S153, pp. 1600-1603.

Singh Manmohan et al., "Nanoparticles and microparticles as vaccine-delivery systems," Expert Review of Vaccines, Oct. 1, 2007, vol. 6, No. 5, pp. 797-808.

Akiko Iwasaki et al., "Toll-like receptor control of the adaptive immune responses," Nature Immunology, Oct. 2004, vol. 5, No. 10, pp. 987-995.

Comanducci M. et al., "*NadA, a novel vaccine candidate of Neisseria meningitidis.*" J. of Experimental Medicine, Jun. 3, 2002, vol. 195, No. 11, pp. 1445-1454.

Zhengrong Cui et al., "Physical characterization and macrophage cell uptake of mannan-coated nanoparticles," Drug Development and Industrial Pharmacy, Jan. 1, 2003, vol. 29, No. 6, pp. 689-700.

Leena Peltonen et al., "The Effect of Cosolvlents on the Formulation of Nanoparticles From Low-Molecular-Weight Poly(I)lactide," AAPS PharmSciTech, 2002, 3 (4): 1-7.

Tobias Jung et al., "Loading of Tetanus Toxoid to Biodegradable Nanoparticles from Branched Poly(Sulfobutyl-Polyvinyl Alcohol)-g-(Lactide-Co-Glycolide) *Nanoparticles by Protein Adsorption: A Mechanistic Study*," Pharmaceutical Research, Aug. 2002, 19 (8): 1105-1113.

Christine Oster, "Microparticular and Nanoparticular DNA Delivery Systems as Adjuvants for DNA immunization," dissertation, University of Marburg, Germany, 2004.

Manmohan Singh, "Anionic Microparticles are a Potent Delivery System for Recombinant Antigens from Neisseria meningitidis Serotype B," Journal of Pharameceutical Sciences, Feb. 2004, vol. 93: 273-282.

Gref, R. et al. "Biodegradable Long-Circulating Polymeric Nanospheres," Science, vol. 263, No. 5153, 1994, pp. 1600-1603.

Cui, Z. et al. "Physical characterization and macrophage cell uptake of mannan-coated nanoparticles," Drug Development and Industrial Pharmacy, vol. 29, No. 6, 2003, pp. 689-700.

Singh, M. et al. "Nanoparticles and microparticles as vaccine-delivery systems," Expert Review of Vaccines, vol. 6, No. 5, 2007, pp. 797-808.

Iwasaki, A. et al. "Toll-like receptor control of the adaptive immune responses," Nature Immunology, vol. 5, No. 10, 2004, pp. 987-995.

Comanducci, M. et al. "NadA, a novel vaccine candidate of Neisseria meningitidis," Journal of Experimental Medicine, vol. 195, No. 11, 2002, pp. 1445-1454.

\* cited by examiner

NANOPARTICLES FOR USE IN PHARMACEUTICAL COMPOSITIONS

BACKGROUND

Particulate carriers are commonly used in the pharmaceutical arts. For example, particulate carriers have been used with adsorbed or entrapped antigens in attempts to elicit adequate immune responses. Such carriers present multiple copies of a selected antigen to the immune system and are believed to promote trapping and retention of antigens in local lymph nodes. The particles can be phagocytosed by macrophages and can enhance antigen presentation through cytokine release.

For example, commonly owned International Publication No. WO 98/33487 and co-pending Pub. No. US 2003/0049298 describe the use of antigen-adsorbed and antigen-encapsulated microparticles to stimulate immunological responses, including cell-mediated immunological responses, as well as methods of making the microparticles. Polymers used to form the microparticles include poly(lactide) and poly(lactide-co-glycolide)(PLG).

Commonly owned International Publication No. WO 00/06123 and WO 01/36599 and U.S. Pat. No. 6,884,435 disclose methods of making microparticles having adsorbed macromolecules, including polynucleotides and polypeptide antigens. The microparticles comprise, for example, a biodegradable polymer and are formed using, for example, cationic, anionic or nonionic detergents. Microparticles containing anionic detergents can be used with positively charged macromolecules, such as polypeptides. Microparticles containing cationic detergents can be used with negatively charged macromolecules, such as DNA. The use of such microparticles to stimulate immunological responses, including cell-mediated immunological responses, is also disclosed.

Commonly owned International Patent Appln. No. PCT/US06/46212 describes sterile-filtered lyophilized nanoparticle compositions which contain at least one biodegradable polymer, at least one surfactant, at least one cryoprotective agent, and at least one antigen. Also disclosed are methods of making and using such compositions and kits supplying such compositions. Nanoparticles are created using the nanoprecipitation method.

SUMMARY OF THE INVENTION

In various aspects of the present invention, nanoparticle compositions are provided which comprise (a) nanoparticles comprising one or more biodegradable polymers and (b) one or more pharmaceuticals associated with the nanoparticles.

In certain embodiments, the nanoparticle compositions are sterile filtered nanoparticle compositions, which may or may not be lyophilized.

In certain embodiments, the nanoparticles within the compositions of the present invention typically have a size distribution in which the Z average and/or the D(v,0.5) value is less than 200 nm, and more typically less than 150 nm and in which the D(v,0.9) is less than 250 nm, and more typically less than 200 nm.

In certain embodiments, the biodegradable polymers within the nanoparticles are synthetic biodegradable polymers, for example, selected from polyesters including poly (α-hydroxy acids) and polycaprolactones, polyorthoesters, polyanhydrides, polycyanoacrylates, and combinations thereof, among others.

In some aspects of the invention, the pharmaceuticals may be immunogenic species.

In certain embodiments, the immunogenic species are species that stimulate an adaptive immune response. For example, the immunogenic species in these embodiments may comprise one or more antigens. Examples of antigens include polypeptide-containing antigens, polysaccharide-containing antigens, and polynucleotide-containing antigens, among others. Antigens can be derived, for example, from tumor cells and from pathogenic organisms such as viruses, bacteria, fungi and parasites, among other sources.

In certain embodiments, the immunogenic species are species that stimulate an innate immune response. For example, the immunogenic species may be an activator of one or more of the following receptors, among others: Toll-like receptors (TLRs), nucleotide-binding oligomerization domain (NOD) proteins, and receptors that induce phagocytosis, such as scavenger receptors, mannose receptors and β-glucan receptors.

In certain embodiments, the immunogenic species may be selected, for example, from one or more of the following immunological adjuvants: bacterial lipopolysaccharides, peptidoglycan, bacterial lipoproteins, bacterial flagellins, imidazoquinoline compounds, immunostimulatory oligo-nucleotides, single-stranded RNA, saponins, lipotechoic acid, ADP-ribosylating toxins and detoxified derivatives thereof, polyphosphazene, muramyl peptides, thiosemicarbazone compounds, tryptanthrin compounds, and lipid A derivatives, among others.

In certain embodiments, the immunogenic species may be selected, for example, from one or more small molecule immunopotentiators. For example, the immunogenic species may be selected from imidazoquinoline compounds such as resimiquod, imiquimod and imidazoquinoline 090, among others.

In certain embodiments, the compositions of the invention optionally comprise at least one surfactant. In some embodiments, the compositions of the invention optionally comprise at least one cryoprotective agent. In some embodiments, the compositions of the invention optionally comprise at least one surfactant and at least one cryoprotective agent. Examples of cryoprotective agents include polyols, carbohydrates and combinations thereof, among others. Examples of surfactants include non-ionic surfactants, cationic surfactants, anionic surfactants, and zwitterionic surfactants, among others. Surfactants and/or cryoprotective agents may be added, for example, to ensure that lyophilized nanoparticles can be resuspended without an unacceptable increase in size (e.g., without significant aggregation).

Other aspects of the invention are directed to methods of producing nanoparticle compositions that comprise at least one biodegradable polymer.

For example, in some embodiments of the invention, nanoparticle compositions are produced from a method that comprises contacting a first liquid that comprises one or more biodegradable polymers dissolved in a first solvent with a second liquid that comprises a second solvent which is miscible with the first solvent while being a non-solvent for the one or more biodegradable polymers, such that nanoparticles are formed. The first and second liquids are contacted under conditions of gentle shaking, preferably with little or no stirring. For example, gentle shaking is implemented using a gyrotory shaker, among other possibilities.

In some embodiments of the invention, nanoparticle compositions are produced from a method that comprises contacting a first liquid that comprises one or more biodegradable polymers dissolved in a first solvent with a second liquid that comprises a buffer and a second solvent which is miscible with the first solvent while being a non-solvent for the one or more biodegradable polymers, such that nanoparticles are formed.

The first solvent may comprise, for example, one or more hydrophilic organic solvent species, which may be selected, for example, from acetone and ethanol, among others. The second solvent may comprise, for example, water, among other possibilities.

In certain of the above embodiments, the first liquid is added to the second liquid in a dropwise fashion, among other possibilities.

In certain embodiments, the nanoparticles are optionally recovered after formation.

In certain embodiments, the nanoparticles are optionally lyophilized after formation.

In certain embodiments, the first solvent is more volatile than the second solvent and is allowed to evaporate.

In certain embodiments, the biodegradable polymer concentration in the first liquid ranges from 0.25% w/v to 5% w/v (e.g., ranging from 0.25% w/v to 0.5% w/v to 1% w/v to 2% w/v to 3% w/v to 5% w/v), more typically from 0.5% w/v to 3% w/v.

Methods such as the foregoing are advantageous, for example, in that the yield for the nanoparticles, based on the amount of biodegradable polymer in the solution that is recovered in the form of nanoparticles, can be high, for example, ranging from 90% to 95% or more.

In some embodiments, one or more pharmaceuticals are added either during or after nanoparticle formation. For example, one or more immunogenic species (e.g., species that stimulate an immune response, for instance, species that stimulate an innate immune response, an adaptive immune response, or a combination of innate and adaptive responses) may be added either during or after nanoparticle formation.

For instance, in certain embodiments, one or more pharmaceuticals may be added to the nanoparticles after their formation. For example, one or more pharmaceuticals may be attached to the nanoparticles (e.g., adsorbed or conjugated to the surface of the nanoparticles) and/or admixed with the nanoparticles in a liquid or solid composition (e.g., in solution, as an aqueous suspension, colyophilized with the nanoparticles, etc.), or otherwise associated with the nanoparticles.

In certain embodiments, one or more pharmaceuticals may be added to the nanoparticles during their formation. For example, in the method described above, the first liquid may further comprise (in addition to one or more biodegradable polymers dissolved in a first solvent) one or more pharmaceuticals, which may be, for example, dissolved or suspended in the first liquid. Consequently, the one or more pharmaceuticals become entrapped in the nanoparticles concurrent with their formation.

In embodiments where the first liquid comprises a pharmaceutical and the second liquid comprises a buffer, the buffer may be selected to maintain the pH of the second liquid at a point where the pharmaceutical is predominantly uncharged.

In embodiments where the first liquid comprises a pharmaceutical, where the second liquid comprises a buffer, and where the pharmaceutical is a proton-accepting pharmaceutical, the buffer may be selected to maintain a pH that is greater than the pKa of the pharmaceutical.

In embodiments where first liquid comprises a pharmaceutical, where the second liquid comprises a buffer, and where the pharmaceutical is a proton donating pharmaceutical, the buffer may be selected to maintain a pH that is less than the pKa of the pharmaceutical.

Where two pharmaceuticals are employed, they can be, for example, attached to or entrapped within the same population of nanoparticles, or attached to or entrapped within separate populations of nanoparticles, among other possibilities.

In certain embodiments, the amount of pharmaceutical provided (relative to the amount of biodegradable polymer) ranges from 0.25% w/w to 5% w/w (e.g., ranging from 0.25% w/w to 0.5% w/w to 1% w/w to 2% w/w to 3% w/w to 5% w/w).

Methods such as the foregoing are advantageous, for example, in that the encapsulation efficiency for the pharmaceutical, can be quite high, for example, ranging from 50% to 60% to 70% to 80% to 90% or more.

Still other aspects of the invention are directed to methods of delivering the nanoparticle compositions of the invention to a host animal (e.g., for therapeutic, prophylactic, or diagnostic purposes). The above described nanoparticles compositions may be used, for example, to stimulate an innate immune response, an adaptive immune response, or both, in a host animal. The host animal is preferably a vertebrate animal. Delivery of the nanoparticle compositions of the invention can be performed by any known method.

These and other aspects, embodiments, and advantages of the present invention will become more readily apparent to those of ordinary skill in the art in view of the disclosure herein.

DETAILED DESCRIPTION OF THE INVENTION

Figure 1:
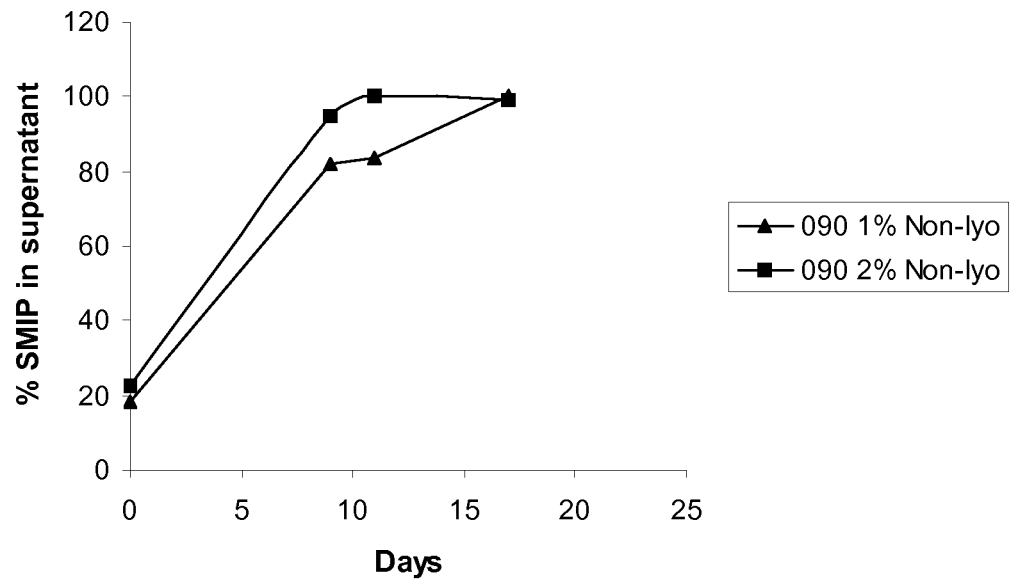
FIG. 1 is a plot of the in vitro release profile of a non-lyophilized suspension at a SMIP concentration 1% and 2% w/w relative to the polymer.

The practice of the present invention will employ, unless otherwise indicated, conventional methods of chemistry, polymer chemistry, biochemistry, molecular biology, immunology and pharmacology, within the skill of the art. Such techniques are explained fully in the literature. See, e.g., *Remington's Pharmaceutical Sciences,* 18th ed. (Easton, Pa.: Mack Publishing Company, 1990); *Methods In Enzymology* (S. Colowick and N. Kaplan, eds., Academic Press, Inc.); Weir, D. M., *Handbook of Experimental Immunology,* Vols. I-IV, 5th ed. (Blackwell Publishers, 1996); Sambrook, J. et al., *Molecular Cloning: A Laboratory Manual,* 3rd ed. (Cold Spring Harbor Laboratory Press, 2001); Ausubel, F. M. et al., *Short Protocols In Molecular Biology,* 5th ed. (Current Protocols, 2002); *Handbook of Surface and Colloidal Chemistry* (Birdi, K. S., ed, CRC Press, 2003) and *Seymour/Carraher's Polymer Chemistry,* 7th ed. (CRC Press, 2007).

All publications, patents and patent applications cited herein, whether supra or infra, are hereby incorporated by reference in their entirety.

As used in this specification and any appended claims, the singular forms "a," "an" and "the" include plural references unless the content clearly dictates otherwise. Thus, for example, the term "nanoparticle" refers to one or more nanoparticles, and the like.

Unless stated otherwise or unless the context clearly dictates otherwise, all percentages and ratios herein are given on a weight basis.

A. Definitions

In describing the present invention, the following terms are intended to be defined as indicated below.

The term "nanoparticle" as used herein, refers to a particle of less than 1,000 nm in diameter.

Particle size can be determined (measured) using methods available in the art. For example, particle size can be determined using photon correlation spectroscopy, dynamic light scattering or quasi-elastic light scattering. These methods are based on the correlation of particle size with diffusion properties of particles obtained from Brownian motion measurements. Brownian motion is the random movement of the particles due to bombardment by the solvent molecules that surround the particles. The larger the particle, the more slowly the Brownian motion will be. Velocity is defined by the translational diffusion coefficient. The value measured refers to how a particle moves within a liquid (hydrodynamic diameter). The diameter that is obtained is the diameter of a sphere that has the same translational diffusion coefficient as the particle.

Particle size can also be determined using static light scattering, which measures the intensity of light scattered by particles in a solution at a single time. Static light scattering measures light intensity as a function of scattering angle and solute concentration. Particles passing though a light source, for example, a laser beam, scatter light at an angle that is inversely proportional to their size. Large particles generate a diffraction pattern at low scattering angles with high intensity, whereas small particles give rise to wide angle low intensity signals. Particle size distributions can be calculated if the intensity of light scattered from a sample are measured as a function of angle. The angular information is compared with a scattering model (e.g., Mie theory) in order to calculate the size distribution.

Generally, particle size is determined at room temperature and involves multiple analyses of the sample in question (e.g., at least 3 repeat measurements on the same sample) to yield an average value for the particle diameter.

For photon correlation spectroscopy, Z average (also called the cumulant mean or hydrodynamic diameter) is typically calculated from cumulants (monomodal) analysis.

For static light scattering measurements (and also for photon correlation spectroscopy in some embodiments), volume-based size parameters may be measured. For instance, the D(v,0.5) (where v means volume) is a size parameter whose value is defined as the point where 50% of the particles (volume basis) in the composition, as measured, have a size that is less than the D(v,0.5) value, and 50% of the particles in the composition have a size that is greater than the D(v,0.5) value. Similarly, the D(v,0.9) is a size parameter whose value is defined as the point where 90% (volume basis) of the particles in the composition have a size that is less than the D(v,0.9) value, and 10% of the particles in the composition have a size that is greater than the D(v,0.9) value.

The nanoparticles within the compositions of the present invention typically have a size distribution in which the Z average and/or the D(v,0.5) value is less than 200 nm, and more typically less than 150 nm and in which the D(v,0.9) is less than 250 nm, and more typically less than 200 nm.

As defined herein, an "organic solvent species" is a solvent species that comprises at least one carbon atom.

As defined herein, an "aqueous" liquid is a water-containing liquid, typically a liquid containing more than 50 wt % water, for example, from 50 to 75 to 90 to 95 wt % or more water.

As defined herein, an "aqueous" solvent is a water-containing solvent, typically a solvent containing more than 50 wt % water, for example, from 50 to 75 to 90 to 95 wt % or more water.

As defined herein, a "nanoparticle suspension" is a liquid phase that contains nanoparticles.

An "aqueous nanoparticle suspension" is a water-containing liquid that further contains nanoparticles. Aqueous nanoparticle suspensions in accordance with the invention typically contain more than 50 wt % water, for example from 50 to 75 to 90 to 95 wt % or more water.

The nanoparticles of the invention are typically formed from polymers that are substantially non-toxic and biodegradable. Such materials include polyesters such as poly($\alpha$-hydroxy acids) and polylactones (e.g., polycaprolactone), polyorthoesters, polyanhydrides, and polycyanoacrylates (e.g., polyalkylcyanoacrylate or "PACA"), among others. More typically, nanoparticles for use with the present invention are polymer nanoparticles derived from poly($\alpha$-hydroxy acids), for example, from a poly(lactide) ("PLA") such as poly(D,L-lactide), a copolymer of lactide and glycolide, such as a poly(D,L-lactide-co-glycolide) or poly(L-lactide-co-glycolide) (both referred to as "PLG"), or a copolymer of D,L-lactide and caprolactone. The polymer nanoparticles may be formed from polymers which have a variety of molecular weights and, in the case of the copolymers, such as PLG, a variety of monomer (e.g., lactide:glycolide) ratios. Polymers are also available in a variety of end groups. These parameters are discussed further below.

The term "surfactant" comes from the phrase "surface active agent". Surfactants accumulate at interfaces (e.g., at liquid-liquid, liquid-solid and/or liquid-gas interfaces) and change the properties of that interface. As used herein, surfactants include detergents, dispersing agents, suspending agents, emulsion stabilizers, and the like.

As defined herein, "carbohydrates" include monosaccharides, oligosaccharides and polysaccharides, as well as substances derived from monosaccharides, oligosaccharides and polysaccharides, for example, by reduction (e.g., alditols), by oxidation of one or more terminal groups to carboxylic acids (e.g., glucuronic acid), or by replacement of one or more hydroxy group(s) by a hydrogen atom or an amino group (e.g., beta-D-glucosamine and beta-D-galactosamine).

As defined herein, a "monosaccharide" is a polyhydric alcohol, i.e., an alcohol that further comprises either an aldehyde group (in which case the monosaccharide is an aldose) or a keto group (in which case the monosaccharide is a ketose). Monosaccharides typically contain from 3-10 carbons. Moreover, monosaccharides commonly have the empirical formula $(CH_2O)_n$ where n is an integer of three or greater, typically 3-10. Examples of 3-6 carbon aldoses include glyceraldehyde, erythrose, threose, ribose, 2-deoxyribose, arabinose, xylose, lyxose, allose, altrose, glucose, mannose, gulose, idose, galactose, and talose. Examples of 3-6 carbon ketoses include dihydroxyacetone, erythrulose, ribulose, xylulose, psicose, fructose, sorbose, and tagatose. Naturally occurring monosaccharides are normally found in the D-isomer form, as opposed to the L-form.

As defined herein "oligosaccharide" refers to a relatively short monosaccharide polymer, i.e., one containing from 2 to 30 monosaccharide units. As defined herein, a "polysaccharide" is a monosaccharide polymer that is beyond oligosaccharide length (i.e., one containing more than 30 monosaccharide units). Moreover, as used herein, the term "polysaccharide" also refers to a monosaccharide polymer that contains two or more linked monosaccharides. To avoid ambiguity, the second definition is to be applied at all times, unless there are explicit indications to the contrary. The term "polysaccharide" also includes polysaccharide derivatives, such as amino-functionalized and carboxyl-functionalized polysaccharide derivatives, among many others. Monosaccharides are typically linked by glycosidic linkages. Specific examples include disaccharides (such as sucrose, lactose, trehalose, maltose, gentiobiose and cellobiose), trisaccharides (such as raffinose), tetrasaccharides (such as stachyose), and pentasaccharides (such as verbascose).

As used herein the term "saccharide" encompasses monosaccharides, oligosaccharides and polysaccharides. A "saccharide-containing species" is a molecule, at least a portion of which is a saccharide. Examples include saccharide cryoprotective agents, saccharide antigens, antigens comprising saccharides conjugated to carrier peptides, and so forth.

As used herein, a "cryoprotective agent" is an agent that protects a composition from experiencing adverse effects upon freezing and thawing. For example, in the present invention, cryoprotective agents may be added to prevent substantial nanoparticle agglomeration from occurring when the lyophilized compositions of the invention are resuspended.

A "polynucleotide" is a nucleic acid polymer. As used herein, a "polynucleotide" can include as few as 5, 6, 7 or 8 nucleotides. Furthermore, a "polynucleotide" can include both double- and single-stranded sequences and refers to, but is not limited to, cDNA from viral, procaryotic or eucaryotic mRNA, genomic RNA and DNA sequences from viral (e.g. RNA and DNA viruses and retroviruses) or procaryotic DNA, and synthetic DNA sequences. The term also captures sequences that include any of the known base analogs of DNA and RNA. The term further includes modifications, such as deletions, additions and substitutions (generally conservative in nature), to a native sequence, for example, where the nucleic acid molecule encodes an antigenic protein. These modifications may be deliberate, as through site-directed mutagenesis, or may be accidental, such as through mutations of hosts that produce antigens.

As defined herein an "oligonucleotide" is a polynucleotide having in the range of 5 to 100 nucleotides, more typically, 5 to 30 nucleotides in size.

As defined herein, a "polynucleotide-containing species" is a molecule, at least a portion of which is a polynucleotide.

The term "polypeptide" refers to a polymer of amino acid residues and is not limited to a minimum length of the product. Thus, proteins, peptides, oligopeptides, dimers, multimers, and the like, are included within the definition. Proteins for use herein include full length proteins and protein fragments. In certain embodiments, modifications to the native sequence, such as deletions, additions and substitutions (generally conservative in nature), are employed.

A "polypeptide-containing species" is a molecule, at least a portion of which is a polypeptide. Examples include polypeptides, glycoproteins, metalloproteins, lipoproteins, saccharide antigens conjugated to carrier proteins, and so forth.

The term "pharmaceutical" refers to biologically active compounds such as antibiotics, antiviral agents, growth factors, hormones, antigens, immunological adjuvants, and the like.

The term "adjuvant" refers to any substance that assists or modifies the action of a pharmaceutical, including but not limited to immunological adjuvants, which increase and/or diversify the immune response to an antigen. Hence, immunological adjuvants are compounds that are capable of potentiating an immune response to antigens. Immunological adjuvants can potentiate humoral and/or cellular immunity. In some embodiments, immunological adjuvants stimulate an innate immune response. Immunological adjuvants may also be referred to herein as "immunopotentiators."

As used herein, an "antigen" refers to a molecule containing one or more epitopes (e.g., linear, conformational or both) that elicit an immunological response. The term may be used interchangeably with the term "immunogen."

As used herein, an "epitope" is that portion of given species (e.g., an antigenic molecule or antigenic complex) that determines its immunological specificity. An epitope is within the scope of the present definition of antigen. Commonly, an epitope is a polypeptide or polysaccharide in a naturally occurring antigen. In artificial antigens, it can be a low molecular weight substance such as an arsanilic acid derivative. Normally, a B-cell epitope will include at least about 5 amino acids but can be as small as 3-4 amino acids. A T-cell epitope, such as a CTL epitope, will typically include at least about 7-9 amino acids, and a helper T-cell epitope will typically include at least about 12-20 amino acids.

The term "antigen" as used herein denotes both subunit antigens, i.e., antigens which are separate and discrete from a whole organism with which the antigen is associated in nature, as well as killed, attenuated or inactivated bacteria, viruses, parasites or other pathogens or tumor cells. Antibodies such as anti-idiotype antibodies, or fragments thereof, and synthetic peptide mimotopes, which can mimic an antigen or antigenic determinant, are also captured under the definition of antigen as used herein. Similarly, an oligonucleotide or polynucleotide that expresses an immunogenic protein, or antigenic determinant in vivo, such as in nucleic acid immunization applications, is also included in the definition of antigen herein.

An "immunological response" or "immune response" to an antigen or composition is the development in a subject of a humoral and/or a cellular immune response to molecules present in the composition of interest.

Immune responses include innate and adaptive immune responses. Innate immune responses are fast-acting responses that provide a first line of defense for the immune system. In contrast, adaptive immunity uses selection and clonal expansion of immune cells having somatically rearranged receptor genes (e.g., T- and B-cell receptors) that recognize antigens from a given pathogen or disorder (e.g., a tumor), thereby providing specificity and immunological memory. Innate immune responses, among their many effects, lead to a rapid burst of inflammatory cytokines and activation of antigen-presenting cells (APCs) such as macrophages and dendritic cells. To distinguish pathogens from self-components, the innate immune system uses a variety of relatively invariable receptors that detect signatures from pathogens, known as pathogen-associated molecular patterns, or PAMPs. The addition of microbial components to experimental vaccines is known to lead to the development of robust and durable adaptive immune responses. The mechanism behind this potentiation of the immune responses has been reported to involve pattern-recognition receptors (PRRs), which are differentially expressed on a variety of immune cells, including neutrophils, macrophages, dendritic cells, natural killer cells, B cells and some nonimmune cells such as epithelial and endothelial cells. Engagement of PRRs leads to the activation of some of these cells and their secretion of cytokines and chemokines, as well as maturation and migration of other cells. In tandem, this creates an inflammatory environment that leads to the establishment of the adaptive immune response. PRRs include nonphagocytic receptors, such as Toll-like receptors (TLRs) and nucleotide-binding oligomerization domain (NOD) proteins, and receptors that induce phagocytosis, such as scavenger receptors, mannose receptors and β-glucan receptors. Reported TLRs (along with examples of some reported ligands, which may be used as immunogenic species in various embodiments of the invention) include the following: TLR1 (bacterial lipoproteins from *Mycobacteria, Neisseria*), TLR2 (zymosan yeast particles, peptidoglycan, lipoproteins, glycolipids, lipopolysaccharide), TLR3 (viral double-stranded RNA, poly:IC), TLR4 (bacterial lipopolysaccharides, plant product taxol), TLR5 (bacterial flagellins), TLR6 (yeast zymosan particles, lipotechoic acid, lipopeptides from mycoplasma), TLR7 (single-stranded RNA, imiquimod, resimiquimod, and other synthetic compounds such as loxoribine and bropirimine), TLR8 (single-stranded RNA, resimiquimod) and TLR9 (CpG oligonucleotides), among others. Dendritic cells are recognized as some of the most important cell types for initiating the priming of naive $CD4^+$ helper T ($T_H$) cells and for inducing $CD8^+$ T cell differentiation into killer cells. TLR signaling has been reported to play an important role in determining the quality of these helper T cell responses, for instance, with the nature of the TLR signal determining the specific type of $T_H$ response that is observed (e.g., $T_H1$ versus $T_H2$ response). A combination of antibody (humoral) and cellular immunity are produced as part of a $T_H1$-type response, whereas a $T_H2$-type response is predominantly an antibody response. Various TLR ligands such as CpG DNA (TLR9) and imidazoquinolines (TLR7, TLR8) have been documented to stimulate cytokine production from immune cells in vitro. The imidazoquinolines are the first small, drug-like compounds shown to be TLR agonists. For further information, see, e.g., A. Pashine, N. M. Valiante and J. B. Ulmer, *Nature Medicine* 11, S63-S68 (2005), K. S. Rosenthal and D. H. Zimmerman, *Clinical and Vaccine Immunology,* 13(8), 821-829 (2006), and the references cited therein.

For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTLs"). CTLs have specificity for peptide antigens that are presented in association with proteins encoded by the major histocompatibility complex (MHC) and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, non-specific effector cells against cells displaying peptide antigens in association with MHC molecules on their surface. A "cellular immune response" also refers to the production of cytokines, chemokines and other such molecules produced by activated T-cells and/or other white blood cells, including those derived from $CD4^+$ and $CD8^+$ T-cells.

A composition such as an immunogenic composition or a vaccine that elicits a cellular immune response may thus serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host. The ability of a particular antigen or composition to stimulate a cell-mediated immunological response may be determined by a number of assays known in the art, such as by lymphoproliferation (lymphocyte activation) assays, CTL cytotoxic cell assays, by assaying for T-lymphocytes specific for the antigen in a sensitized subject, or by measurement of cytokine production by T cells in response to restimulation with antigen. Such assays are well known in the art. See, e.g., Erickson et al. (1993) *J. Immunol.* 151:4189-4199; Doe et al. (1994) *Eur. J. Immunol.* 24:2369-2376. Thus, an immunological response as used herein may be one which stimulates the production of CTLs and/or the production or activation of helper T-cells. The antigen of interest may also elicit an antibody-mediated immune response. Hence, an immunological response may include, for example, one or more of the following effects among others: the production of antibodies by, for example, B-cells; and/or the activation of suppressor T-cells and/or γδ T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art.

Immunogenic compositions in accordance with the present invention display "enhanced immunogenicity" for a given antigen when they possess a greater capacity to elicit an immune response than the immune response elicited by an equivalent amount of the antigen in a differing composition (e.g., wherein the antigen is administered as a soluble protein). Thus, a composition may display "enhanced immunogenicity," for example, because the composition generates a stronger immune response, or because a lower dose or fewer doses of antigen is necessary to achieve an immune response in the subject to which it is administered. Such enhanced immunogenicity can be determined, for example, by administering the compositions of the invention, and antigen controls, to animals and comparing assay results of the two.

As used herein, "treatment" (including variations thereof, for example, "treat" or "treated") refers to any of (i) the prevention of a pathogen or disorder in question (e.g. cancer or a pathogenic infection, as in a traditional vaccine), (ii) the reduction or elimination of symptoms associated with a pathogen or disorder in question, and (iii) the substantial or complete elimination of a pathogen or disorder in question. Treatment may thus be effected prophylactically (prior to arrival of the pathogen or disorder in question) or therapeutically (following arrival of the same).

The terms "effective amount" or "pharmaceutically effective amount" of a pharmaceutical composition of the present invention refer herein to a sufficient amount of the immunogenic composition to treat or diagnose a condition of interest. The exact amount required will vary from subject to subject, depending, for example, on the species, age, and general condition of the subject; the severity of the condition being treated; in the case of an immunological response, the capacity of the subject's immune system to synthesize antibodies, for example, and the degree of protection desired; and the mode of administration; among other factors. An appropriate "effective" amount in any individual case may be determined by one of ordinary skill in the art. Thus, a "therapeutically effective amount" will typically fall in a relatively broad range that can be determined through routine trials.

By "vertebrate subject" or "vertebrate animal" is meant any member of the subphylum cordata, including, without limitation, mammals such as cattle, sheep, pigs, goats, horses, and humans; domestic animals such as dogs and cats; and birds, including domestic, wild and game birds such as cocks and hens including chickens, turkeys and other gallinaceous birds. The term does not denote a particular age. Thus, both adult and newborn animals are covered.

By "pharmaceutically acceptable" or "pharmacologically acceptable" is meant a material which is not biologically or otherwise undesirable, e.g., the material may be administered to an individual without causing any excessively undesirable biological effects in the individual or interacting in an excessively deleterious manner with any of the components of the composition in which it is contained.

The term "excipient" refers to any essentially accessory substance that may be present in the finished dosage form. For example, the term "excipient" includes vehicles, binders, disintegrants, fillers (diluents), lubricants, suspending/dispersing agents, and so forth.

By "physiological pH" or a "pH in the physiological range" is meant a pH in the range of approximately 7.2 to 8.0 inclusive, more typically in the range of approximately 7.2 to 7.6 inclusive.

As used herein, the phrase "vector construct" generally refers to any assembly that is capable of directing the expression of a nucleic acid sequence(s) or gene(s) of interest. A "DNA vector construct" refers to a DNA molecule that is capable of directing the expression of a nucleic acid sequence (s) or gene(s) of interest. One specific type of DNA vector construct is a plasmid, which is a circular episomal DNA molecule capable of autonomous replication within a host cell. Typically, a plasmid is a circular double stranded DNA loop into which additional DNA segments can be ligated. pCMV is one specific plasmid that is well known in the art. Other DNA vector constructs are known, which are based on RNA viruses. These DNA vector constructs typically comprise a promoter that functions in a eukaryotic cell, 5' of a cDNA sequence for which the transcription product is an RNA vector construct (e.g., an alphavirus RNA vector replicon), and a 3' termination region. Other examples of vector constructs include RNA vector constructs (e.g., alphavirus vector constructs) and the like. As used herein, "RNA vector construct", "RNA vector replicon" and "replicon" refer to an RNA molecule that is capable of directing its own amplification or self-replication in vivo, typically within a target cell. The RNA vector construct is used directly, without the requirement for introduction of DNA into a cell and transport to the nucleus where transcription would occur. By using the RNA vector for direct delivery into the cytoplasm of the host cell, autonomous replication and translation of the heterologous nucleic acid sequence occurs efficiently.

B. General Methods

As indicated above, in various aspects of the invention, nanoparticle compositions are provided which comprise (a) nanoparticles comprising at least one biodegradable polymer and (b) at least one pharmaceutical associated with the nanoparticles. Much of the following discussion is directed to immunogenic species as exemplary pharmaceuticals. However, the invention is not so-limited.

Other aspects of the invention are directed to methods of producing nanoparticle compositions that comprise at least one biodegradable polymer.

1. Nanoparticle Compositions

Useful polymers for forming nanoparticles compositions in accordance with the present invention include homopolymers, copolymers and polymer blends, both natural and synthetic. Such polymers may be derived, for example, from homopolymers and copolymers of the following: poly(alpha-hydroxy acids) including polyglycolic acid (PGA) (also known as polyglycolide), polylactic acid (PLA) (also known as polylactide) and polyhydroxybutyric acid (also known as polyhydroxybutyrate); polydioxanone; polycaprolactone; polyorthoesters; polycyanoacrylates, polyanhydrides; and combinations thereof. More typical are poly(α-hydroxy acids) such as poly(L-lactide), poly(D,L-lactide) (both referred to as "PLA" herein), copolymers of lactide and glycolide, such as poly(L-lactide-co-glycolide) and poly(D,L-lactide-co-glycolide) (both designated as "PLG" herein).

The above polymers are available in a variety of molecular weights, and the appropriate molecular weight for a given use is readily determined by one of skill in the art. Thus, for example, a suitable molecular weight for PLA may be on the order of about 2000 to 5000. A suitable molecular weight for PLG may range from about 5,000 to about 200,000.

Where copolymers are employed, copolymers with a variety of monomer ratios may be available. For example, where PLG is used to form the nanoparticles, a variety of lactide:glycolide molar ratios will find use herein, and the ratio is largely a matter of choice, depending in part on any coadministered species (e.g., adsorbed, entrapped, or otherwise associated with the nanoparticles) and the rate of degradation desired. For example, a 50:50 PLG polymer, containing 50% lactide and 50% glycolide, will provide a faster resorbing copolymer, while 75:25 PLG degrades more slowly, and 85:15 and 90:10, even more slowly, due to the increased lactide component. Mixtures of nanoparticles with varying lactide:glycolide ratios may also find use herein in order to achieve the desired release kinetics. Degradation rate of the nanoparticles of the present invention can also be controlled by such factors as polymer molecular weight and polymer crystallinity.

Where used PLG copolymers are typically those having a lactide/glycolide molar ratio ranging, for example, from 10:90 to 20:80 to 25:75 to 40:60 to 45:55 to 55:45 to 60:40 to 75:25 to 80:20 to 90:10, and having a molecular weight ranging, for example, from 5,000 to 10,000 to 20,000 to 40,000 to 50,000 to 70,000 to 100,000 to 200,00 Daltons, among others.

PLG copolymers are also available with a variety of end groups, including acid end groups and ester end groups.

PLG copolymers with varying lactide:glycolide ratios, molecular weights and end groups are readily available commercially from a number of sources including from Boehringer Ingelheim, Germany, Birmingham Polymers, Inc., Birmingham, Ala., USA and Lakeshore Biomaterials, Birmingham, Ala., USA. Some exemplary PLG copolymers, available from Boehringer Ingelheim, include: (a) RG 502, a PLG having predominantly alkyl ester end groups on one of the chain ends, a 50:50 lactide/glycolide molar ratio and a molecular weight of 12,000 Da, (b) RG 503, a PLG having predominantly alkyl ester end groups on one of the chain ends, a 50:50 lactide/glycolide molar ratio and a molecular weight of 34,000 Da, (c) RG 504, a PLG having predominantly alkyl ester end groups on one of the chain ends, a 50:50 lactide/glycolide molar ratio and a molecular weight of 48,000 Da, (d) RG 752, a PLG having predominantly alkyl ester end groups on one of the chain ends, a 75:25 lactide/glycolide molar ratio and a molecular weight of 22,000 Da, (e) RG 755, a PLG having predominantly alkyl ester end groups on one of the chain ends, a 75:25 lactide/glycolide molar ratio and a molecular weight of 68,000 Da, (f) RG 502H, a PLG having a 50:50 lactide/glycolide molar ratio, and having predominantly free carboxyl end groups on one of the chain ends, and (g) RG 503H, a PLG having a 50:50 lactide/glycolide molar ratio, and having predominantly free carboxyl end groups on one of the chain ends.

Nanoparticles in accordance with the invention can be prepared using various suitable methods.

In certain embodiments of the invention, a first liquid that comprises one or more biodegradable polymers dissolved in a first solvent is contacted with a second liquid that comprises a second solvent which is miscible with the first solvent while being a non-solvent for the one or more biodegradable polymers, such that nanoparticles are formed.

In certain of these embodiments, the second solvent is an aqueous solvent.

In certain embodiments, the second liquid comprises a buffer.

In certain embodiments, the first liquid may be contacted with the second liquid by a variety of suitable techniques, with the general idea being that the two liquids are combined with minimal intermixing. For example, the first liquid may be carefully poured onto the second liquid, or the first liquid may be gently injected into or onto the second liquid, among other possibilities. In one embodiment the first liquid is added in a drop-wise fashion to the surface of the second liquid.

In certain embodiments, during or after bringing the first and second liquids into contact, the liquids are allowed to interact with one another under conditions of gentle agitation (e.g., gentle shaking, preferably with little or no stirring), or under conditions of no agitation whatsoever, to yield nanoparticles. Gentle shaking may be implemented, for example, using a gyrotory shaker, among other possibilities.

It has been found that combining the liquids with gentle shaking can result in particles with uniform size distribution at higher yields than are obtained with stirring. For example, the yield, based on the amount of biodegradable polymer that is recovered in the form of nanoparticles, is higher with the method in which the liquids are combined with shaking (e.g., ranging from 90% or more) than the yield with the method in which the liquids are combined with stirring (e.g., 60% or less).

The first and second liquids may be combined in any suitable relative volume. For example, the first and second liquids may be combined relative volumes selected from 1:10 to 1:5 to 1:2 to 1:1 to 2:1 to 5:1 to 10:1, more typically from 1:2 to 2:1, even more typically about 1:1.

The biodegradable polymer concentration in the first liquid may be set at any suitable level, but typically ranges from 0.25% w/v to 5% w/v (e.g., ranging from 0.25% w/v to 0.5% w/v to 1% w/v to 2% w/v to 3% w/v to 4% w/v to 5% w/v), more typically 0.5% w/v to 3% w/v. In general, the polymer concentration will affect the particle size, with lower concentrations yielding lower particle sizes. The polymer concentration may also affect the encapsulation efficiency of any pharmaceuticals that are introduced during the nanoparticle formation process.

The first solvent may comprise, for instance, one or more organic solvent species, for example, one or more hydrophilic organic solvent species which may be selected from acetone and ethanol, among many others.

The second solvent may comprise, for example, water and/or one or more hydrophilic organic solvent species, among other possibilities. For instance, the second liquid may be selected from deionized water, normal saline, and buffered solutions. The latter solutions can (a) provide a tonicity, i.e., osmolality, that is essentially the same as normal physiological fluids and (b) maintain a pH compatible with normal physiological conditions. In other embodiments, the tonicity and/or pH characteristics of the compositions of the present invention may be adjusted after nanoparticle formation.

The second liquid may also comprise a buffer, for instance, to enhance encapsulation efficiency. Buffers are available which can maintain the pH of the second liquid within a desired pH range when the first and second liquids are brought into contact with one another. For example, buffers are commercially available which are designed to maintain pH values ranging from 2 or less to 3 to 4 to 5 to 6 to 7 to 8 to 9 to 10 to 11 to 12 or more. The following are a few examples of commercially available buffers (available from Sigma-Aldrich and/or Polysciences Inc.): citrate buffer solution (pH~4.8), sodium acetate buffer (pH~5.2, pH~7.0), phosphate citrate buffer (pH~5.0), SSC buffer (pH~7.0), PBS (pH~7.2 to 7.5), SSPE buffer (pH~7.4), Tris buffered saline (pH~7.4), Tris-phosphate-EDTA (pH~8.0), triethylammonium bicarbonate buffer (pH~8.0), Tris-EDTA (pH~8.0), Tris-borate-EDTA (pH~8.3), Tris-glycine (pH~8.3), Tris acetate-EDTA (pH~8.3), triethylammonium bicarbonate buffer (pH~8.5), Tris-glycine-SDS Buffer (pH~8.6), glycine buffer solution (pH~9.2), and sodium bicarbonate-sodium carbonate buffer (pH~9.6), among others.

In certain embodiments, the first solvent is more volatile that the second solvent. In these embodiments, the first solvent may be removed, for example, by evaporation under ambient conditions or by evaporation under reduced pressure and/or elevated temperature.

In some embodiments, one or more additional species are added during or after nanoparticles formation. Such additional species can include, for instance, pharmaceuticals such as immunogenic species (e.g., species that stimulate an innate immune response, species that stimulate an adaptive immune response, or both, including immunological adjuvants, immunopotentiators, and antigens), surfactants, cryoprotective agents, and other supplemental components such as tonicity adjusting agents, pH adjusting agents, and so forth.

In these embodiments, the one or more additional species may be entrapped within the nanoparticles, associated with the surfaces of the nanoparticles (e.g., adsorbed or conjugated to the surfaces of the nanoparticles), admixed with the nanoparticles in a liquid or solid composition (e.g., provided in solution, as an aqueous suspension, colyophilized with the nanoparticles, etc.), and/or otherwise associated with the nanoparticles.

In some embodiments of the invention, one or more additional species are added during the above-described method of nanoparticles formation. For instance, the first liquid, the second liquid, or both, may contain additional species as desired.

As a specific example, in addition to one or more biodegradable polymers dissolved in an organic solvent, the first liquid may further comprise one or more pharmaceuticals (which may be, for example, dissolved or suspended in the first liquid). Consequently, the one or more pharmaceuticals become entrapped in the nanoparticles.

In certain of these embodiments, the second liquid may comprise a buffer. The buffer may be selected, for example, to maintain the pH of the second liquid at a point where the pharmaceutical is predominantly uncharged. In embodiments where the pharmaceutical is a proton-accepting pharmaceutical, the buffer may be selected, for example, to maintain a pH that is greater than the pKa of the pharmaceutical. In embodiments where the pharmaceutical is a proton donating pharmaceutical, the buffer may be selected to maintain a pH that is less than the pKa of the pharmaceutical.

In certain embodiments, the amount of pharmaceutical provided (e.g., immunogenic species, etc.) ranges from 0.25% w/w to 5% w/w relative to the amount of biodegradable polymer used in the process (e.g., ranging from 0.25% w/w to 0.5% w/w to 1% w/w to 2% w/w to 3% w/w to 4% w/w to 5% w/w).

Where the pharmaceutical is added to the first liquid, for polymer concentrations ranging from 0.5% w/v to 3% w/v (5 g/ml to 30 g/ml) in the first liquid, a range of 0.5% w/w to 3% w/w for the pharmaceutical relative the amount of polymer corresponds to overall concentrations in the first liquid ranging from 0.0025% w/v to 0.09% w/v (i.e., 25 to 900 micrograms per mL, more typically 100 to 600 micrograms per mL).

Methods such as the foregoing are advantageous, for example, in that the encapsulation efficiency for the pharmaceutical can be quite high, for example, ranging from 50% to 60% to 70% to 80% to 90% or more.

Vigorous agitation upon combining the first and second liquids (e.g., stirring with a magnetic stir bar), in the absence of a buffer in the second liquid, result in much lower encapsulation efficiencies.

In some embodiments of the invention, one or more additional species are added subsequent to nanoparticle formation (and typically subsequent to organic solvent removal, as well as subsequent to washing steps, if any). For example, pharmaceuticals such as immunogenic species (e.g., antigens, immunological adjuvants, immunopotentiators, etc.), agents for adjusting tonicity and/or pH, surfactants, cryoprotective agents, and so forth, may be added subsequent to nanoparticle formation. Frequently, these additional species are added to the nanoparticles as an aqueous solution or dispersion. The resulting admixture may be lyophilized in some embodiments.

As noted above, the additional species may be associated with the surfaces of the nanoparticles (e.g., adsorbed or conjugated to the surfaces of the nanoparticles) and/or otherwise associated or non-associated with the nanoparticles to varying degrees (e.g., admixed with the nanoparticles in a liquid dispersion, in a solid composition, etc.), among other possibilities.

Where two pharmaceuticals (e.g., immunogenic species, etc.) are employed, they can be, for example, attached to (e.g., adsorbed or conjugated to) or entrapped within the same population of nanoparticles, or attached to or entrapped within separate populations of nanoparticles, among other possibilities.

Compositions in accordance with some embodiments of the invention can be sterile filtered (e.g., using a 200 micron filter) at any time after nanoparticle formation, for example, after nanoparticle formation but before the addition of any additional species, after nanoparticle formation and after the addition of any additional species, and so forth.

The nanoparticles within the compositions of the present invention (including lyophilized compositions that have been resuspended) typically have a size distribution in which the Z average and/or the D(v,0.5) value is less than 200 nm, and more typically less than 150 nm and in which the D(v,0.9) is less than 250 nm, and more typically less than 200 nm.

Taking as an example nanoparticles formed using PLG, there are several advantages of the techniques of the present invention, as compared with microparticle forming techniques based on oil-in-water and water-in-oil-in-water emulsification. A first benefit is the ease of preparation. The nanoparticle method is a single step technique and does not need high-shear homogenization as does the microparticle method, only gentle shaking. In addition, the entire emulsion-based microparticle particle preparation process is typically aseptic, whereas, due to their small size, nanoparticles may be sterile filtered post particle preparation, leading to less strict production requirements.

Furthermore, the type of organic solvent used with the two methods is different. The nanoparticle method can be performed using acetone whereas the microparticle method typically involves the use of dichloromethane (DCM) as a solvent. The U.S. Food and Drug Administration (FDA) classifies DCM as a Class 2 solvent and has established limits on the amounts of allowable residual solvent which may be present in pharmaceutical products, whereas acetone is a Class 3 solvent for which the FDA has established higher limits on the allowable amounts.

2. Immunological Adjuvants

As previously indicated, one or more immunological adjuvants may optionally be provided in the compositions of the invention. They may be, for example, entrapped within the nanoparticles, associated with the surfaces of the nanoparticles (e.g., adsorbed or conjugated to the surfaces of the nanoparticles) and/or otherwise associated with the nanoparticles to varying degrees (e.g., admixed with the nanoparticles in a liquid suspension, admixed with the nanoparticles in a solid composition, for instance, colyophilized with the nanoparticles, etc.), among other possibilities Immunological adjuvants for use with the invention include, but are not limited to, one or more of the following:

a. Mineral Containing Compositions

Mineral containing compositions suitable for use as adjuvants include mineral salts, such as aluminum salts and calcium salts. The invention includes mineral salts such as hydroxides (e.g. oxyhydroxides), phosphates (e.g. hydroxyphosphates, orthophosphates), sulfates, etc. (see, e.g., *Vaccine Design: The Subunit and Adjuvant Approach* (Powell, M. F. and Newman, M. J. eds.) (New York: Plenum Press) 1995, Chapters 8 and 9), or mixtures of different mineral compounds (e.g. a mixture of a phosphate and a hydroxide adjuvant, optionally with an excess of the phosphate), with the compounds taking any suitable form (e.g. gel, crystalline, amorphous, etc.), and with adsorption to the salt(s) being preferred. The mineral containing compositions may also be formulated as a particle of metal salt (WO 00/23105).

Aluminum salts may be included in vaccines of the invention such that the dose of $Al^{3+}$ is between 0.2 and 1.0 mg per dose.

In one embodiment, the aluminum based adjuvant for use in the present invention is alum (aluminum potassium sulfate ($AlK(SO_4)_2$)), or an alum derivative, such as that formed in-situ by mixing an antigen in phosphate buffer with alum, followed by titration and precipitation with a base such as ammonium hydroxide or sodium hydroxide.

Another aluminum-based adjuvant for use in vaccine formulations of the present invention is aluminum hydroxide adjuvant ($Al(OH)_3$) or crystalline aluminum oxyhydroxide (AlOOH), which is an excellent adsorbant, having a surface area of approximately 500 $m^2/g$. In another embodiment, the aluminum based adjuvant is aluminum phosphate adjuvant ($AlPO_4$) or aluminum hydroxyphosphate, which contains phosphate groups in place of some or all of the hydroxyl groups of aluminum hydroxide adjuvant. Preferred aluminum phosphate adjuvants provided herein are amorphous and soluble in acidic, basic and neutral media.

In another embodiment, the adjuvant comprises both aluminum phosphate and aluminum hydroxide. In a more particular embodiment thereof, the adjuvant has a greater amount of aluminum phosphate than aluminum hydroxide, such as a ratio of 2:1, 3:1, 4:1, 5:1, 6:1, 7:1, 8:1, 9:1 or greater than 9:1, by weight aluminum phosphate to aluminum hydroxide. In another embodiment, aluminum salts in the vaccine are present at 0.4 to 1.0 mg per vaccine dose, or 0.4 to 0.8 mg per vaccine dose, or 0.5 to 0.7 mg per vaccine dose, or about 0.6 mg per vaccine dose.

Generally, the preferred aluminum-based adjuvant(s), or ratio of multiple aluminum-based adjuvants, such as aluminum phosphate to aluminum hydroxide is selected by optimization of electrostatic attraction between molecules such that the antigen carries an opposite charge as the adjuvant at the desired pH. For example, aluminum phosphate adjuvant (iep=4) adsorbs lysozyme, but not albumin at pH 7.4. Should albumin be the target, aluminum hydroxide adjuvant would be selected (iep 11.4). Alternatively, pretreatment of alumib. Oil-Emulsions Oil-emulsion compositions and formulations suitable for use as adjuvants (with or without other specific immunostimulating agents such as muramyl peptides or bacterial cell wall components) include squalene-water emulsions, such as MF59 (5% Squalene, 0.5% Tween 80, and 0.5% Span 85, formulated into submicron particles using a microfluidizer). See WO 90/14837. See also, Podda (2001) *Vaccine* 19: 2673-2680; Frey et al. (2003) *Vaccine* 21:4234-4237. MF59 is used as the adjuvant in the FLUAD™ influenza virus trivalent subunit vaccine.

Particularly preferred oil-emulsion adjuvants for use in the compositions are submicron oil-in-water emulsions. Preferred submicron oil-in-water emulsions for use herein are squalene/water emulsions optionally containing varying amounts of MTP-PE, such as a submicron oil-in-water emulsion containing 4-5% w/v squalene, 0.25-1.0% w/v Tween 80™ (polyoxyethylenesorbitan monooleate), and/or 0.25-1.0% Span 85™ (sorbitan trioleate), and, optionally, N-acetylmuramyl-L-alanyl-D-isogluatminyl-L-alanine-2-(1'-2'-dipalmitoyl-sn-glycero-3-huydroxyphosphophoryloxy)-ethylamine (MTP-PE), for example, the submicron oil-in-water emulsion known as "MF59" (WO 90/14837; U.S. Pat. No. 6,299,884; U.S. Pat. No. 6,451,325; and Ott et al., "MF59—Design and Evaluation of a Safe and Potent Adjuvant for Human Vaccines" in *Vaccine Design: The Subunit and Adjuvant Approach* (Powell, M. F. and Newman, M. J. eds.) (New York: Plenum Press) 1995, pp. 277-296). MF59 contains 4-5% w/v Squalene (e.g. 4.3%), 0.25-0.5% w/v Tween 80™, and 0.5% w/v Span 85™ and optionally contains various amounts of MTP-PE, formulated into submicron particles using a microfluidizer such as Model 110Y microfluidizer (Microfluidics, Newton, Mass.). For example, MTP-PE may be present in an amount of about 0-500 μg/dose, more preferably 0-250 μg/dose and most preferably, 0-100 μg/dose. As used herein, the term "MF59-0" refers to the above submicron oil-in-water emulsion lacking MTP-PE, while the term MF59-MTP denotes a formulation that contains MTP-PE. For instance, "MF59-100" contains 100 μg MTP-PE per dose, and so on. MF69, another submicron oil-in-water emulsion for use herein, contains 4.3% w/v squalene, 0.25% w/v Tween 80™, and 0.75% w/v Span 85™ and optionally MTP-PE. Yet another submicron oil-in-water emulsion is MF75, also known as SAF, containing 10% squalene, 0.4% Tween 80™, 5% pluronic-blocked polymer L121, and thr-MDP, also microfluidized into a submicron emulsion. MF75-MTP denotes an MF75 formulation that includes MTP, such as from 100-400 μg MTP-PE per dose.

Submicron oil-in-water emulsions, methods of making the same and immunostimulating agents, such as muramyl peptides, for use in the compositions, are described in detail in WO 90/14837; U.S. Pat. Nos. 6,299,884; and 6,451,325.

Complete Freund's adjuvant (CFA) and incomplete Freund's adjuvant (IFA) may also be used as adjuvants in the invention.

c. Saponin Formulations

Saponin formulations are also suitable for use as adjuvants in the invention. Saponins are a heterologous group of sterol glycosides and triterpenoid glycosides that are found in the bark, leaves, stems, roots and even flowers of a wide range of plant species. Saponins isolated from the bark of the *Quillaia saponaria* Molina tree have been widely studied as adjuvants. Saponins can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. Saponin adjuvant formulations include STIMULON® adjuvant (Antigenics, Inc., Lexington, Mass.). Saponin compositions have been purified using High Performance Thin Layer Chromatography (HP-TLC) and Reversed Phase High Performance Liquid Chromatography (RP-HPLC). Specific purified fractions using these techniques have been identified, including QS7, QS17, QS18, QS21, QH-A, QH-B and QH-C. Preferably, the saponin is QS21. A method of production of QS21 is disclosed in U.S. Pat. No. 5,057,540. Saponin formulations may also comprise a sterol, such as cholesterol (see WO 96/33739).

Combinations of saponins and cholesterols can be used to form unique particles called Immunostimulating Complexes (ISCOMs). ISCOMs typically also include a phospholipid such as phosphatidylethanolamine or phosphatidylcholine. Any known saponin can be used in ISCOMs. Preferably, the ISCOM includes one or more of Quil A, QHA and QHC. ISCOMs are further described in EP 0 109 942, WO 96/11711 and WO 96/33739. Optionally, the ISCOMS may be devoid of (an) additional detergent(s). See WO 00/07621.

A review of the development of saponin based adjuvants can be found in Barr et al. (1998) *Adv. Drug Del. Rev.* 32:247-271. See also Sjolander et al. (1998) *Adv. Drug Del. Rev.* 32:321-338.

d. Virosomes and Virus Like Particles (VLPs)

Virosomes and Virus Like Particles (VLPs) are also suitable as adjuvants. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1). VLPs are discussed further in WO 03/024480; WO 03/024481; Niikura et al. (2002) *Virology* 293:273-280; Lenz et al. (2001) *J. Immunol.* 166(9): 5346-5355; Pinto et al. (2003) *J. Infect. Dis.* 188:327-338; and Gerber et al. (2001) *J. Virol.* 75(10):4752-4760. Virosomes are discussed further in, for example, Gluck et al. (2002) *Vaccine* 20:B10-B16. Immunopotentiating reconstituted influenza virosomes (IRIV) are used as the subunit antigen delivery system in the intranasal trivalent INFLEXAL™ product (Mischler and Metcalfe (2002) *Vaccine* 20 Suppl 5:B17-B23) and the INFLUVAC PLUS™ product.

e. Bacterial or Microbial Derivatives

Adjuvants suitable for use in the invention include bacterial or microbial derivatives such as:

(1) Non-toxic derivatives of enterobacterial lipopolysaccharide (LPS): Such derivatives include Monophosphoryl lipid A (MPL) and 3-O-deacylated MPL (3dMPL). 3dMPL is a mixture of 3 De-O-acylated monophosphoryl lipid A with 4, 5 or 6 acylated chains. A preferred "small particle" form of 3 De-O-acylated monophosphoryl lipid A is disclosed in EP 0 689 454. Such "small particles" of 3dMPL are small enough to be sterile filtered through a 0.22 micron membrane (see EP 0 689 454). Other non-toxic LPS derivatives include monophosphoryl lipid A mimics, such as aminoalkyl glucosaminide phosphate derivatives, e.g., RC-529. See Johnson et al. (1999) *Bioorg. Med. Chem. Lett.* 9:2273-2278.

(2) Lipid A Derivatives: Lipid A derivatives include derivatives of lipid A from *Escherichia coli* such as OM-174. OM-174 is described for example in Meraldi et al. (2003) *Vaccine* 21:2485-2491; and Pajak et al. (2003) *Vaccine* 21:836-842.

(3) Immunostimulatory oligonucleotides: Immunostimulatory oligonucleotides or polymeric molecules suitable for use as adjuvants in the invention include nucleotide sequences containing a CpG motif (a sequence containing an unmethylated cytosine followed by guanosine and linked by a phosphate bond). Bacterial double stranded RNA or oligonucleotides containing palindromic or poly(dG) sequences have also been shown to be immunostimulatory. The CpG's can include nucleotide modifications/analogs such as phosphorothioate modifications and can be double-stranded or single-stranded. Optionally, the guanosine may be replaced with an analog such as 2'-deoxy-7-deazaguanosine. See Kandimalla et al. (2003) *Nucl. Acids Res.* 31(9): 2393-2400; WO 02/26757; and WO 99/62923 for examples of possible analog substitutions. The adjuvant effect of CpG oligonucleotides is further discussed in Krieg (2003) *Nat. Med.* 9(7):831-835; McCluskie et al. (2002) *FEMS Immunol. Med. Microbiol.* 32:179-185; WO 98/40100; U.S. Pat. No. 6,207,646; U.S. Pat. Nos. 6,239,116; and 6,429,199. The CpG sequence may be directed to TLR9, such as the motif GTCGTT or TTCGTT. See Kandimalla et al. (2003) *Biochem. Soc. Trans.* 31 (part 3):654-658. The CpG sequence may be specific for inducing a Th1 immune response, such as a CpG-A ODN, or it may be more specific for inducing a B cell response, such a CpG-B ODN. CpG-A and CpG-B ODNs are discussed in Blackwell et al. (2003) *J. Immunol.* 170(8):4061-4068; Krieg (2002) *TRENDS Immunol.* 23(2): 64-65; and WO 01/95935. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, Kandimalla et al. (2003) *BBRC* 306:948-953; Kandimalla et al. (2003) *Biochem. Soc. Trans.* 31(part 3):664-658; Bhagat et al. (2003) *BBRC* 300:853-861; and WO03/035836.

Immunostimulatory oligonucleotides and polymeric molecules also include alternative polymer backbone structures such as, but not limited to, polyvinyl backbones (Pitha et al. (1970) *Biochem. Biophys. Acta* 204(1):39-48; Pitha et al. (1970) *Biopolymers* 9(8):965-977), and morpholino backbones (U.S. Pat. Nos. 5,142,047; 5,185,444). A variety of other charged and uncharged polynucleotide analogs are known in the art. Numerous backbone modifications are known in the art, including, but not limited to, uncharged linkages (e.g., methyl phosphonates, phosphotriesters, phosphoamidates, and carbamates) and charged linkages (e.g., phosphorothioates and phosphorodithioates).

(4) ADP-ribosylating toxins and detoxified derivatives thereof: Bacterial ADP-ribosylating toxins and detoxified derivatives thereof may be used as adjuvants in the invention. Preferably, the protein is derived from *E. coli* (i.e., *E. coli* heat labile enterotoxin "LT"), cholera ("CT"), or pertussis ("PT"). The use of detoxified ADP-ribosylating toxins as mucosal adjuvants is described in WO 95/17211 and as parenteral adjuvants in WO 98/42375. Preferably, the adjuvant is a detoxified LT mutant such as LT-K63, LT-R72, and LTR192G. The use of ADP-ribosylating toxins and detoxified derivatives thereof, particularly LT-K63 and LT-R72, as adjuvants can be found in the following references: Beignon et al. (2002) *Infect. Immun.* 70(6):3012-3019; Pizza et al. (2001) *Vaccine* 19:2534-2541; Pizza et al. (2000) *Int. J. Med. Microbiol.* 290(4-5):455-461; Scharton-Kersten et al. (2000) *Infect. Immun.* 68(9):5306-5313; Ryan et al. (1999) *Infect. Immun.* 67(12):6270-6280; Partidos et al. (1999) *Immunol. Lett.* 67(3):209-216; Peppoloni et al. (2003) *Vaccines* 2(2):285-293; and Pine et al. (2002) *J. Control Release* 85(1-3):263-270. Numerical reference for amino acid substitutions is preferably based on the alignments of the A and B subunits of ADP-ribosylating toxins set forth in Domenighini et al. (1995) *Mol. Microbiol.* 15(6):1165-1167.

f. Bioadhesives and Mucoadhesives

Bioadhesives and mucoadhesives may also be used as adjuvants. Suitable bioadhesives include esterified hyaluronic acid microspheres (Singh et al. (2001) *J. Cont. Release* 70:267-276) or mucoadhesives such as cross-linked derivatives of polyacrylic acid, polyvinyl alcohol, polyvinyl pyrollidone, polysaccharides and carboxymethylcellulose. Chitosan and derivatives thereof may also be used as adjuvants in the invention (see WO 99/27960).

g. Liposomes

Examples of liposome formulations suitable for use as adjuvants are described in U.S. Pat. Nos. 6,090,406; 5,916,588; and EP Patent Publication No. EP 0 626 169.

h. Polyoxyethylene Ether and Polyoxyethylene Ester Formulations

Adjuvants suitable for use in the invention include polyoxyethylene ethers and polyoxyethylene esters (see, e.g., WO 99/52549). Such formulations further include polyoxyethylene sorbitan ester surfactants in combination with an octoxynol (WO 01/21207) as well as polyoxyethylene alkyl ethers or ester surfactants in combination with at least one additional non-ionic surfactant such as an octoxynol (WO 01/21152).

Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

i. Polyphosphazene (PCPP)

PCPP formulations suitable for use as adjuvants are described, for example, in Andrianov et al. (1998) *Biomaterials* 19(1-3):109-115; and Payne et al. (1998) *Adv. Drug Del. Rev.* 31(3):185-196.

j. Muramyl Peptides

Examples of muramyl peptides suitable for use as adjuvants include N-acetyl-muramyl-L-threonyl-D-isoglutamine (thr-MDP), N-acetyl-normuramyl-1-alanyl-d-isoglutamine (nor-MDP), and N-acetylmuramyl-1-alanyl-d-isoglutaminyl-1-alanine-2-(1'-2'-dipalmitoyl-sn-glycero-3-hydroxyphosphoryloxy)-ethylamine MTP-PE).

k. Imidazoquinoline Compounds

Examples of imidazoquinoline compounds suitable for use as adjuvants include Imiquimod and its analogues, which are described further in Stanley (2002) *Clin. Exp. Dermatol.* 27(7):571-577; Jones (2003) *Curr. Opin. Investig. Drugs* 4(2):214-218; and U.S. Pat. Nos. 4,689,338; 5,389,640; 5,268,376; 4,929,624; 5,266,575; 5,352,784; 5,494,916; 5,482,936; 5,346,905; 5,395,937; 5,238,944; and 5,525,612.

Preferred imidazoquinolines are those of the formula,

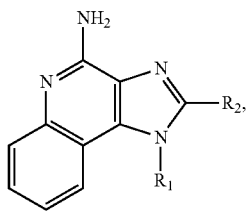

where $R_1$ and $R_2$ are independently selected from the group consisting of hydrogen, alkyl of one to ten carbon atoms, hydroxyalkyl of one to ten carbon atoms, alkoxyalkyl of one to ten carbon atoms, acyloxyalkyl wherein the acyloxy moiety is alkanoyloxy of one to five carbon atoms or benzoyloxy and wherein the alkyl moiety contains one to six carbon atoms,

wherein $R_3$ and $R_4$ are independently selected from the group consisting of hydrogen and alkyl of one to ten carbon atoms, benzyl, (phenyl)ethyl and phenyl, where the benzyl, (phenyl)ethyl or phenyl substituent are optionally substituted on the benzene ring by one or two moieties independently selected from the group consisting of alkyl of one to four carbon atoms, alkoxy of one to four carbon atoms and halogen. The preceding alkyl groups may be linear, branched and/or cyclic. Particularly preferred imidazoquinolines for the practice of the present invention include imiquimod, resiquimod, and

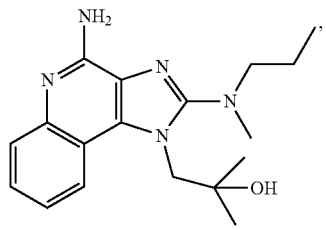 [SMILES: CCCN(C)c1nc2c(N)nc3ccccc3c2n1CC(C)(C)O]

the latter of which is also referred to herein as "imidazoquinoline 090". See, e.g., Int. Pub. Nos. WO 2006/031878 to Valiante et al. and WO 2007/109810 to Sutton et al.

l. Thiosemicarbazone Compounds

Examples of thiosemicarbazone compounds suitable for use as adjuvants, as well as methods of formulating, manufacturing, and screening for such compounds, include those described in WO 04/60308. The thiosemicarbazones are particularly effective in the stimulation of human peripheral blood mononuclear cells for the production of cytokines, such as TNF-α.

m. Tryptanthrin Compounds

Examples of tryptanthrin compounds suitable for use as adjuvants, as well as methods of formulating, manufacturing, and screening for such compounds, include those described in WO 04/64759. The tryptanthrin compounds are particularly effective in the stimulation of human peripheral blood mononuclear cells for the production of cytokines, such as TNF-α.

n. Human Immunomodulators

Human immunomodulators suitable for use as adjuvants include cytokines, such as interleukins (e.g. IL-1, IL-2, IL-4, IL-5, IL-6, IL-7, IL-12, etc.), interferons (e.g. interferon-γ), macrophage colony stimulating factor (M-CSF), and tumor necrosis factor (TNF).

The invention may also comprise combinations of aspects of one or more of the adjuvants identified above. For example, the following adjuvant compositions may be used in the invention:

(1) a saponin and an oil-in-water emulsion (WO 99/11241);
(2) a saponin (e.g., QS21)+a non-toxic LPS derivative (e.g. 3dMPL) (see WO 94/00153);
(3) a saponin (e.g., QS21)+a non-toxic LPS derivative (e.g. 3dMPL)+a cholesterol;
(4) a saponin (e.g., QS21)+3dMPL+IL-12 (optionally+a sterol) (WO 98/57659);
(5) combinations of 3dMPL with, for example, QS21 and/or oil-in-water emulsions (see EP 0 835 318; EP 0 735 898; and EP 0 761 231);
(6) SAF, containing 10% Squalane, 0.4% Tween 80, 5% pluronic-block polymer L121, and thr-MDP, either microfluidized into a submicron emulsion or vortexed to generate a larger particle size emulsion;
(7) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™);
(8) one or more mineral salts (such as an aluminum salt)+a non-toxic derivative of LPS (such as 3dPML);
(9) one or more mineral salts (such as an aluminum salt)+an immunostimulatory oligonucleotide (such as a nucleotide sequence including a CpG motif).

3. Antigens

As previously indicated, one or more antigens may optionally be provided in the compositions of the invention. Antigens may be entrapped within the nanoparticles, associated with the surfaces of the nanoparticles (e.g., adsorbed or conjugated to the surfaces of the nanoparticles) and/or otherwise associated with the nanoparticles to varying degrees (e.g., admixed with the nanoparticles in a liquid suspension, admixed with the nanoparticles in a solid composition, for instance, colyophilized with the nanoparticles), among other possibilities.

Each antigen may be provided in an effective amount (e.g., an amount effective for use in therapeutic, prophylactic, or diagnostic methods in accordance with the invention). For example, the compositions of the present invention may be used to treat or prevent infections caused by any of the below-listed pathogens.

Antigens for use with the invention include, but are not limited to, one or more of the following antigens set forth below, or antigens derived from one or more of the pathogens set forth below:

a. Bacterial Antigens

Bacterial antigens suitable for use in the invention include proteins, polysaccharides, lipopolysaccharides, and outer membrane vesicles which may be isolated, purified or derived from a bacterium. In addition, bacterial antigens include bacterial lysates and inactivated bacteria formulations. Bacteria antigens can be produced by recombinant expression. Bacterial antigens preferably include epitopes which are exposed on the surface of the bacteria during at least one stage of its life cycle. Bacterial antigens are preferably conserved across multiple serotypes. Bacterial antigens include antigens derived from one or more of the bacteria set forth below as well as the specific antigens examples identified below.

*Neisseria meningitides*: Meningitides antigens include proteins (such as those identified in WO99/24578; WO99/36544; WO99/57280; WO00/22430; Tettelin et al. (2000) *Science* 287:1809-1815; WO96/29412; and Pizza et al. (2000) *Science* 287:1816-1820), saccharides (including a polysaccharide, oligosaccharide or lipopolysaccharide), or outer-membrane vesicles (WO 01/52885; Bjune et al. (1991) *Lancet* 338(8775):1093-1096; Fuskasawa et al. (1999) *Vaccine* 17:2951-2958; and Rosenqist et al. (1998) *Dev. Biol. Strand* 92:323-333) purified or derived from *N. meningitides* serogroup such as A, C, W135, Y, and/or B. *Meningitides* protein antigens can be selected from adhesions, autotransporters, toxins, Fe acquisition proteins, and membrane associated proteins (preferably integral outer membrane protein).

*Streptococcus pneumoniae*: *Streptococcus pneumoniae* antigens include a saccharide (including a polysaccharide or an oligosaccharide) and/or protein from *Streptococcus pneumoniae*. Saccharide antigens can be selected from serotypes 1, 2, 3, 4, 5, 6B, 7F, 8, 9N, 9V, 10A, 11A, 12F, 14, 15B, 17F, 18C, 19A, 19F, 20, 22F, 23F, and 33F. Protein antigens can be selected from a protein identified in WO 98/18931; WO 98/18930; U.S. Pat. No. 6,699,703; U.S. Pat. No. 6,800,744; WO 97/43303; and WO 97/37026. *Streptococcus pneumoniae* proteins can be selected from the Poly Histidine Triad family (PhtX), the Choline Binding Protein family (CbpX), CbpX truncates, LytX family, LytX truncates, CbpX truncate-LytX truncate chimeric proteins, pneumolysin (Ply), PspA, PsaA, Sp128, Sp101, Sp130, Sp125 or Sp133.

*Streptococcus pyogenes* (Group A *Streptococcus*): Group A *Streptococcus* antigens include proteins identified in WO 02/34771 and WO 2005/032582 (including GAS 40), fusions of fragments of GAS M proteins (including those described in WO 02/094851; and Dale (1999) *Vaccine* 17:193-200, and Dale (1996) *Vaccine* 14(10): 944-948), fibronectin binding protein (Sfb1), Streptococcal heme-associated protein (Shp), and Streptolysin S (SagA).

*Moraxella catarrhalis*: *Moraxella* antigens include antigens identified in WO 02/18595; and WO 99/58562, outer membrane protein antigens (HMW-OMP), C-antigen, and/or LPS.

*Bordetella pertussis*: Pertussis antigens include petussis holotoxin (PT) and filamentous haemagglutinin (FHA) from *B. pertussis*, optionally also combination with pertactin and/or agglutinogens 2 and 3 antigen.

*Staphylococcus aureus*: Staph aureus antigens include *S. aureus* type 5 and 8 capsular polysaccharides optionally conjugated to nontoxic recombinant *Pseudomonas aeruginosa*exotoxin A, such as StaphVAX™, and antigens derived from surface proteins, invasins (leukocidin, kinases, hyaluronidase), surface factors that inhibit phagocytic engulfment (capsule, Protein A), carotenoids, catalase production, Protein A, coagulase, clotting factor, and membrane-damaging toxins (optionally detoxified) that lyse eukaryotic cell membranes (hemolysins, leukotoxin, leukocidin).

*Staphylococcus epidermis*: *S. epidermidis* antigens include slime-associated antigen (SAA).

*Clostridium tetani* (Tetanus): Tetanus antigens include tetanus toxoid (TT), preferably used as a carrier protein in conjunction/conjugated with the compositions of the present invention.

*Cornynebacterium diphtheriae* (Diphtheria): Diphtheria antigens include diphtheria toxin, preferably detoxified, such as $CRM_{197}$. Additionally, antigens capable of modulating, inhibiting or associated with ADP ribosylation are contemplated for combination/co-administration/conjugation with the compositions of the present invention. The diphtheria toxoids may be used as carrier proteins.

*Haemophilus influenzae* B (Hib): Hib antigens include a Hib saccharide antigen.

*Pseudomonas aeruginosa*: *Pseudomonas* antigens include endotoxin A, Wzz protein, *P. aeruginosa* LPS, more particularly LPS isolated from PAO1 (O5 serotype), and Outer Membrane Proteins, including Outer Membrane Proteins F (OprF) (Price et al. (2001) *Infect Immun.* 69(5):3510-3515).

*Legionella pneumophila*. Bacterial antigens can be derived from *Legionella pneumophila*.

*Streptococcus agalactiae* (Group B *Streptococcus*): Group B *Streptococcus* antigens include protein and saccharide antigens, such as those identified in WO 02/34771; WO 03/093306; WO 04/041157; and WO 2005/002619 (including proteins GBS 80, GBS 104, GBS 276 and GBS 322, and including saccharide antigens derived from serotypes Ia, Ib, Ia/c, II, III, IV, V, VI, VII and VIII).

*Neisserria gonorrhoeae*: Gonorrhoeae antigens include Por (or porin) protein, such as PorB (see, e.g., Zhu et al. (2004) *Vaccine* 22:660-669), a transferring binding protein, such as TbpA and TbpB (see, e.g., Price et al. (2004) *Infect. Immun.* 71(1):277-283), an opacity protein (such as Opa), a reduction-modifiable protein (Rmp), and outer membrane vesicle (OMV) preparations (see, e.g., Plante et al. (2000) *J. Infect. Dis.* 182:848-855); WO 99/24578; WO 99/36544; WO 99/57280; and WO02/079243).

*Chlamydia trachomatis*: *Chlamydia trachomatis* antigens include antigens derived from serotypes A, B, Ba and C (agents of trachoma, a cause of blindness), serotypes $L_1$, $L_2$ & $L_3$ (associated with Lymphogranuloma venereum), and serotypes, D-K. *Chlamydia* trachomas antigens also include antigens identified in WO 00/37494; WO 03/049762; WO 03/068811; and WO 05/002619, including PepA (CT045), LcrE (CT089), ArtJ (CT381), DnaK (CT396), CT398, OmpH-like (CT242), L7/L12 (CT316), OmcA (CT444), AtosS (CT467), CT547, Eno (CT587), HrtA (CT823), and MurG (CT761).

*Treponema pallidum* (Syphilis): Syphilis antigens include TmpA antigen.

*Haemophilus ducreyi* (causing chancroid): *Ducreyi* antigens include outer membrane protein (DsrA).

*Enterococcus faecalis* or *Enterococcus faecium*: Antigens include a trisaccharide repeat and other *Enterococcus* derived antigens provided in U.S. Pat. No. 6,756,361.

*Helicobacter pylori*: H pylori antigens include Cag, Vac, Nap, HopX, HopY and urease antigen.

*Staphylococcus saprophyticus*: Antigens include the 160 kDa hemagglutinin of *S. saprophyticus* antigen.

*Yersinia enterocolitica* Antigens include LPS (Xu et al. (2002) *Infect. Immun.* 70(8): 4414-4423).

*E. coli*: *E. coli* antigens can be derived from enterotoxigenic *E. coli* (ETEC), enteroaggregative *E. coli* (EAggEC), diffusely adhering *E. coli* (DAEC), enteropathogenic *E. coli* (EPEC), or enterohemorrhagic *E. coli* (EHEC).

*Bacillus anthracis* (anthrax): *B. anthracis* antigens are optionally detoxified and can be selected from A-components (lethal factor (LF) and edema factor (EF)), both of which can share a common B-component known as protective antigen (PA). In certain embodiments, the compositions of the present invention do not include an anthrax antigen.

*Yersinia pestis* (plague): Plague antigens include F1 capsular antigen (Gosfeld et al. (2003) *Infect. Immun.* 71(1)): 374-383), LPS (Fields et al. (1999) *Infect. Immun.* 67(10): 5395-5408), *Yersinia pestis* V antigen (Hill et al. (1997) *Infect. Immun.* 65(11): 4476-4482).

*Mycobacterium tuberculosis: Tuberculosis* antigens include lipoproteins, LPS, BCG antigens, a fusion protein of antigen 85B (Ag85B) and ESAT-6 optionally formulated in cationic lipid vesicles (Olsen et al. (2004) *Infect. Immun.* 72(10): 6148-6150), *Mycobacterium tuberculosis* (Mtb) isocitrate dehydrogenase associated antigens (Banerjee et al. (2004) *Proc. Natl. Acad. Sci. USA* 101(34):12652-12657), and MPT51 antigens (Suzuki et al. (2004) *Infect. Immun.* 72(7):3829-3837).

*Rickettsia*: Antigens include outer membrane proteins, including the outer membrane protein A and/or B (OmpB) (Chao et al. (2004) *Biochim. Biophys. Acta.* 1702(2):145-152), LPS, and surface protein antigen (SPA) (Carl et al. (1989) *J. Autoimmun.* 2 Suppl:81-91).

*Listeria monocytogenes*. Bacterial antigens can be derived from *Listeria monocytogenes*.

*Chlamydia pneumoniae*: Antigens include those identified in WO 02/02606.

*Vibrio cholerae*: Antigens include proteinase antigens, LPS, particularly lipopolysaccharides of *Vibrio cholerae* II, O1 Inaba O-specific polysaccharides, *V. cholera* O139, antigens of IEM108 vaccine (Liang et al. (2003) *Infect. Immun.* 71(10):5498-5504), and Zonula occludens toxin (Zot).

*Salmonella typhi* (typhoid fever): Antigens include capsular polysaccharides preferably conjugates (Vi, i.e. vax-TyVi).

*Borrelia burgdorferi* (Lyme disease): Antigens include lipoproteins (such as OspA, OspB, Osp C and Osp D), other surface proteins such as OspE-related proteins (Erps), decorin-binding proteins (such as DbpA), and antigenically variable VI proteins, such as antigens associated with P39 and P13 (an integral membrane protein, Noppa et al. (2001) *Infect. Immun.* 69(5):3323-3334), VlsE Antigenic Variation Protein (Lawrenz et al. (1999) *J. Clin. Microbiol.* 37(12): 3997-4004).

*Porphyromonas gingivalis*: Antigens include *P. gingivalis* outer membrane protein (OMP).

*Klebsiella*: Antigens include OMPs, including OMP A, and polysaccharides optionally conjugated to tetanus toxoid.

Other bacterial antigens include capsular antigens, polysaccharide antigens or protein antigens of any of the above. Further bacterial antigens also include outer membrane vesicle (OMV) preparations. Additionally, antigens include live, attenuated, and/or purified versions of any of the aforementioned bacteria. Antigens can be derived from gram-negative or gram-positive bacteria. Antigens can be derived from aerobic or anaerobic bacteria.

Additionally, any of the above bacterial-derived saccharides (polysaccharides, LPS, LOS or oligosaccharides) can be conjugated to another agent or antigen, such as a carrier protein (for example $CRM_{197}$). Such conjugation can be direct conjugation effected by reductive amination of carbonyl moieties on the saccharide to amino groups on the protein, as provided in U.S. Pat. No. 5,360,897; and Roy et al. (1984) *Can. J. Biochem. Cell Biol.* 62(5):270-275. In another embodiment, the saccharides can be conjugated through a linker, such as, with succinamide or other linkages provided in Hermanson, G. T., *Bioconjugate Techniques,* 1st ed., Academic Press (1996) and Wong, S. S., *CRC, Chemistry of Protein Conjugation and Cross-Linking,* 1st ed., CRC-Press (1991).

b. Viral Antigens

Viral antigens suitable for use in the invention include inactivated (or killed) virus, attenuated virus, split virus formulations, purified subunit formulations, viral proteins which may be isolated, purified or derived from a virus, and Virus Like Particles (VLPs). Viral antigens can be derived from viruses propagated on cell culture or other substrate or expressed recombinantly. Viral antigens preferably include epitopes which are exposed on the surface of the virus during at least one stage of its life cycle. Viral antigens are preferably conserved across multiple serotypes or isolates. Viral antigens include antigens derived from one or more of the viruses set forth below as well as the specific antigens examples identified below.

Orthomyxovirus: Viral antigens may be derived from an Orthomyxovirus, such as Influenza A, B and C. Orthomyxovirus antigens may be selected from one or more of the viral proteins, including hemagglutinin (HA), neuraminidase (NA), nucleoprotein (NP), matrix protein (M1), membrane protein (M2), one or more of the transcriptase components (PB1, PB2 and PA). Preferred antigens include HA and NA.

Influenza antigens may be derived from interpandemic (annual) flu strains. Influenza antigens may be derived from strains with the potential to cause pandemic a pandemic outbreak (i.e., influenza strains with new haemagglutinin compared to the haemagglutinin in currently circulating strains, or influenza strains which are pathogenic in avian subjects and have the potential to be transmitted horizontally in the human population, or influenza strains which are pathogenic to humans). Influenza antigens may be derived from viruses grown in eggs or cell culture.

Paramyxoviridae viruses: Viral antigens may be derived from Paramyxoviridae viruses, such as Pneumoviruses (RSV), Paramyxoviruses (PIV) and Morbilliviruses (Measles).

Pneumovirus: Viral antigens may be derived from a Pneumovirus, such as Respiratory syncytial virus (RSV), Bovine respiratory syncytial virus, Pneumonia virus of mice, and Turkey rhinotracheitis virus. Preferably, the Pneumovirus is RSV. Pneumovirus antigens may be selected from one or more of the following proteins, including surface proteins Fusion (F), Glycoprotein (G) and Small Hydrophobic protein (SH), matrix proteins M and M2, nucleocapsid proteins N, P and L and nonstructural proteins NS1 and NS2. Preferred Pneumovirus antigens include F, G and M. See e.g., Johnstone et al. (2004) *J. Gen. Virol.* 85(Pt 11):3229-3238). Pneumovirus antigens may also be formulated in or derived from chimeric viruses. For example, chimeric RSV/PIV viruses may comprise components of both RSV and PIV.

Paramyxovirus: Viral antigens may be derived from a Paramyxovirus, such as Parainfluenza virus types 1-4 (PIV), Mumps, Sendai viruses, Simian virus 5, Bovine parainfluenza virus and Newcastle disease virus. Preferably, the Paramyxovirus is PIV or Mumps. Paramyxovirus antigens may be selected from one or more of the following proteins: Hemagglutinin Neuraminidase (HN), Fusion proteins F1 and F2, Nucleoprotein (NP), Phosphoprotein (P), Large protein (L), and Matrix protein (M). Preferred Paramyxovirus proteins include HN, F1 and F2. Paramyxovirus antigens may also be formulated in or derived from chimeric viruses. For example, chimeric RSV/PIV viruses may comprise components of both RSV and PIV. Commercially available mumps vaccines include live attenuated mumps virus, in either a monovalent form or in combination with measles and rubella vaccines (MMR).

Morbillivirus: Viral antigens may be derived from a Morbillivirus, such as Measles. Morbillivirus antigens may be selected from one or more of the following proteins: hemagglutinin (H), Glycoprotein (G), Fusion factor (F), Large protein (L), Nucleoprotein (NP), Polymerase phosphoprotein (P), and Matrix (M). Commercially available measles vaccines include live attenuated measles virus, typically in combination with mumps and rubella (MMR).

Picornavirus: Viral antigens may be derived from Picornaviruses, such as Enteroviruses, Rhinoviruses, Heparnavirus, Cardioviruses and Aphthoviruses. Antigens derived from Enteroviruses, such as Poliovirus are preferred.

Enterovirus: Viral antigens may be derived from an Enterovirus, such as Poliovirus types 1, 2 or 3, Coxsackie A virus types 1 to 22 and 24, Coxsackie B virus types 1 to 6, Echovirus (ECHO) virus) types 1 to 9, 11 to 27 and 29 to 34 and Enterovirus 68 to 71. Preferably, the Enterovirus is poliovirus. Enterovirus antigens are preferably selected from one or more of the following Capsid proteins VP1, VP2, VP3 and VP4. Commercially available polio vaccines include Inactivated Polio Vaccine (IPV) and Oral poliovirus vaccine (OPV).

Heparnavirus: Viral antigens may be derived from a Heparnavirus, such as Hepatitis A virus (HAV). Commercially available HAV vaccines include inactivated HAV vaccine.

Togavirus: Viral antigens may be derived from a Togavirus, such as a Rubivirus, an Alphavirus, or an Arterivirus. Antigens derived from Rubivirus, such as Rubella virus, are preferred. Togavirus antigens may be selected from E1, E2, E3, C, NSP-1, NSPO-2, NSP-3 and NSP-4. Togavirus antigens are preferably selected from E1, E2 and E3. Commercially available Rubella vaccines include a live cold-adapted virus, typically in combination with mumps and measles vaccines (MMR).

Flavivirus: Viral antigens may be derived from a Flavivirus, such as Tick-borne encephalitis (TBE), Dengue (types 1, 2, 3 or 4), Yellow Fever, Japanese encephalitis, West Nile encephalitis, St. Louis encephalitis, Russian spring-summer encephalitis, Powassan encephalitis. Flavivirus antigens may be selected from PrM, M, C, E, NS-1, NS-2a, NS2b, NS3, NS4a, NS4b, and NS5. Flavivirus antigens are preferably selected from PrM, M and E. Commercially available TBE vaccine include inactivated virus vaccines.

Pestivirus: Viral antigens may be derived from a Pestivirus, such as Bovine viral diarrhea (BVDV), Classical swine fever (CSFV) or Border disease (BDV).

Hepadnavirus: Viral antigens may be derived from a Hepadnavirus, such as Hepatitis B virus. Hepadnavirus antigens may be selected from surface antigens (L, M and S), core antigens (HBc, HBe). Commercially available HBV vaccines include subunit vaccines comprising the surface antigen S protein.

Hepatitis C virus: Viral antigens may be derived from a Hepatitis C virus (HCV). HCV antigens may be selected from one or more of E1, E2, E1/E2, NS345 polyprotein, NS 345-core polyprotein, core, and/or peptides from the nonstructural regions (Houghton et al. (1991) *Hepatology* 14:381-388).

Rhabdovirus: Viral antigens may be derived from a Rhabdovirus, such as a Lyssavirus (Rabies virus) and Vesiculovirus (VSV). Rhabdovirus antigens may be selected from glycoprotein (G), nucleoprotein (N), large protein (L) and nonstructural proteins (NS). Commercially available Rabies virus vaccine comprise killed virus grown on human diploid cells or fetal rhesus lung cells.

Caliciviridae: Viral antigens may be derived from Caliciviridae, such as Norwalk virus, and Norwalk-like Viruses, such as Hawaii Virus and Snow Mountain Virus.

Coronavirus: Viral antigens may be derived from a Coronavirus, SARS, Human respiratory coronavirus, Avian infectious bronchitis (IBV), Mouse hepatitis virus (MHV), and Porcine transmissible gastroenteritis virus (TGEV). Coronavirus antigens may be selected from spike (S), envelope (E), matrix (M), nucleocapsid (N), and Hemagglutinin-esterase glycoprotein (HE). Preferably, the Coronavirus antigen is derived from a SARS virus. SARS viral antigens are described in WO 04/92360;

Retrovirus: Viral antigens may be derived from a Retrovirus, such as an Oncovirus, a Lentivirus or a Spumavirus. Oncovirus antigens may be derived from HTLV-1, HTLV-2 or HTLV-5. Lentivirus antigens may be derived from HIV-1 or HIV-2. Retrovirus antigens may be selected from gag, pol, env, tax, tat, rex, rev, nef, vif, vpu, and vpr. HIV antigens may be selected from gag (p24gag and p55gag), env (gp160 and gp41), pol, tat, nef, rev vpu, miniproteins, (preferably p55 gag and gp140v delete). HIV antigens may be derived from one or more of the following strains: $HIV_{IIIb}$, $HIV_{SF2}$, $HIV_{LAV}$, $HIV_{LAI}$, $HIV_{MN}$, $HIV-1_{CM235}$, $HIV-1_{US4}$.

Reovirus: Viral antigens may be derived from a Reovirus, such as an Orthoreovirus, a Rotavirus, an Orbivirus, or a Coltivirus. Reovirus antigens may be selected from structural proteins $\lambda 1$, $\lambda 2$, $\lambda 3$, $\mu 1$, $\mu 2$, $\sigma 1$, $\sigma 2$, or $\sigma 3$, or nonstructural proteins $\sigma NS$, $\mu NS$, or $\sigma 1s$. Preferred Reovirus antigens may be derived from a Rotavirus. Rotavirus antigens may be selected from VP1, VP2, VP3, VP4 (or the cleaved product VP5 and VP8), NSP 1, VP6, NSP3, NSP2, VP7, NSP4, or NSP5. Preferred Rotavirus antigens include VP4 (or the cleaved product VP5 and VP8), and VP7.

Parvovirus: Viral antigens may be derived from a Parvovirus, such as Parvovirus B19. Parvovirus antigens may be selected from VP-1, VP-2, VP-3, NS-1 and NS-2. Preferably, the Parvovirus antigen is capsid protein VP-2.

Delta hepatitis virus (HDV): Viral antigens may be derived HDV, particularly δ-antigen from HDV (see, e.g., U.S. Pat. No. 5,378,814).

Hepatitis E virus (HEV): Viral antigens may be derived from HEV.

Hepatitis G virus (HGV): Viral antigens may be derived from HGV.

Human Herpesvirus: Viral antigens may be derived from a Human Herpesvirus, such as Herpes Simplex Viruses (HSV), Varicella-zoster virus (VZV), Epstein-Barr virus (EBV), Cytomegalovirus (CMV), Human Herpesvirus 6 (HHV6), Human Herpesvirus 7 (HHV7), and Human Herpesvirus 8 (HHV8). Human Herpesvirus antigens may be selected from immediate early proteins (α), early proteins (β), and late proteins (γ). HSV antigens may be derived from HSV-1 or HSV-2 strains. HSV antigens may be selected from glycoproteins gB, gC, gD and gH, fusion protein (gB), or immune escape proteins (gC, gE, or gI). VZV antigens may be selected from core, nucleocapsid, tegument, or envelope proteins. A live attenuated VZV vaccine is commercially available. EBV antigens may be selected from early antigen (EA) proteins, viral capsid antigen (VCA), and glycoproteins of the membrane antigen (MA). CMV antigens may be selected from capsid proteins, envelope glycoproteins (such as gB and gH), and tegument proteins Papovaviruses: Antigens may be derived from Papovaviruses, such as Papillomaviruses and Polyomaviruses. Papillomaviruses include HPV serotypes 1, 2, 4, 5, 6, 8, 11, 13, 16, 18, 31, 33, 35, 39, 41, 42, 47, 51, 57, 58, 63 and 65. Preferably, HPV antigens are derived from serotypes 6, 11, 16 or 18. HPV antigens may be selected from capsid proteins (L1) and (L2), or E1-E7, or fusions thereof. HPV antigens are preferably formulated into virus-like particles (VLPs). Polyomavirus viruses include BK virus and JK virus. Polyomavirus antigens may be selected from VP1, VP2 or VP3.

Other antigens, compositions, methods, and microbes for use in the invention are described in Plotkin, S. A. et al., *Vaccines*, $4^{th}$ ed., W.B. Saunders Co. (2004); Murray, P. R. et al., *Medical Microbiology* $5^{th}$ ed., Mosby Elsevier (2005);

Joklik, W. K. (ed.), *Virology*, 3rd ed., Appleton & Lange (1988); Howley, P. M. et al. (eds.), *Fundamental Virology*, 4th ed., Lippincott Williams & Wilkins (1991); and Fields, B. N. et al. (eds.), *Fields Virology*, 4th ed., Lippincott Williams & Wilkins (2001).

c. Fungal Antigens

Fungal antigens for use in the invention can be derived from one or more of the fungi set forth below.

Fungal antigens may be derived from Dermatophytres, including: *Epidermophyton floccusum, Microsporum audouini, Microsporum canis, Microsporum distortum, Microsporum equinum, Microsporum gypsum, Microsporum nanum, Trichophyton concentricum, Trichophyton equinum, Trichophyton gallinae, Trichophyton gypseum, Trichophyton megnini, Trichophyton mentagrophytes, Trichophyton quinckeanum, Trichophyton rubrum, Trichophyton schoenleini, Trichophyton tonsurans, Trichophyton verrucosum, T. verrucosum* var. album, var. discoides, var. ochraceum, *Trichophyton violaceum*, and/or *Trichophyton faviforme*.

Fungal pathogens may be derived from *Aspergillus fumigatus, Aspergillus flavus, Aspergillus niger, Aspergillus nidulans, Aspergillus terreus, Aspergillus sydowi, Aspergillus flavatus, Aspergillus glaucus, Blastoschizomyces capitatus, Candida albicans, Candida enolase, Candida tropicalis, Candida glabrata, Candida krusei, Candida parapsilosis, Candida stellatoidea, Candida kusei, Candida parakwsei, Candida lusitaniae, Candida pseudotropicalis, Candida guilliermondi, Cladosporium carrionii, Coccidioides immitis, Blastomyces dermatidis, Cryptococcus neoformans, Geotrichum clavatum, Histoplasma capsulatum, Klebsiella pneumoniae, Paracoccidioides brasiliensis, Pneumocystis carinii, Pythiumn insidiosum, Pityrosporum ovale, Saccharomyces cerevisae, Saccharomyces boulardii, Saccharomyces pombe, Scedosporium apiosperum, Sporothrix schenckii, Trichosporon beigelii, Toxoplasma gondii, Penicillium marneffei, Malassezia* spp., *Fonsecaea* spp., *Wangiella* spp., *Sporothrix* spp., *Basidiobolus* spp., *Conidiobolus* spp., *Rhizopus* spp, *Mucor* spp, *Absidia* spp, *Mortierella* spp, *Cunninghamella* spp, *Saksenaea* spp., *Alternaria* spp, *Curvularia* spp, *Helminthosporium* spp, *Fusarium* spp, *Aspergillus* spp, *Penicillium* spp, *Monolinia* spp, *Rhizoctonia* spp, *Paecilomyces* spp, *Pithomyces* spp, and *Cladosporium* spp.

Processes for producing a fungal antigens are well known in the art (see U.S. Pat. No. 6,333,164). In a preferred method, a solubilized fraction extracted and separated from an insoluble fraction obtainable from fungal cells of which cell wall has been substantially removed or at least partially removed, characterized in that the process comprises the steps of: obtaining living fungal cells; obtaining fungal cells of which cell wall has been substantially removed or at least partially removed; bursting the fungal cells of which cell wall has been substantially removed or at least partially removed; obtaining an insoluble fraction; and extracting and separating a solubilized fraction from the insoluble fraction.

d. STD Antigens

The compositions of the invention can include one or more antigens derived from a sexually transmitted disease (STD). Such antigens can provide for prophylactis or therapy for STDs such as chlamydia, genital herpes, hepatits (such as HCV), genital warts, gonorrhoea, syphilis and/or chancroid (see WO 00/15255). Antigens may be derived from one or more viral or bacterial STDs. Viral STD antigens for use in the invention may be derived from, for example, HIV, herpes simplex virus (HSV-1 and HSV-2), human papillomavirus (HPV), and hepatitis (HCV). Bacterial STD antigens for use in the invention may be derived from, for example, *Neiserria gonorrhoeae, Chlamydia trachomatis, Treponema pallidum, Haemophilus ducreyi, E. coli*, and *Streptococcus agalactiae*. Examples of specific antigens derived from these pathogens are described above.

e. Respiratory Antigens

The compositions of the invention can include one or more antigens derived from a pathogen which causes respiratory disease. For example, respiratory antigens may be derived from a respiratory virus such as Orthomyxoviruses (influenza), Pneumovirus (RSV), Paramyxovirus (PIV), Morbillivirus (measles), Togavirus (Rubella), VZV, and Coronavirus (SARS). Respiratory antigens may be derived from a bacteria which causes respiratory disease, such as *Streptococcus pneumoniae, Pseudomonas aeruginosa, Bordetella pertussis, Mycobacterium tuberculosis, Mycoplasma pneumoniae, Chlamydia pneumoniae, Bacillus anthracis*, and *Moraxella catarrhalis*. Examples of specific antigens derived from these pathogens are described above.

f. Pediatric Vaccine Antigens

The compositions of the invention may include one or more antigens suitable for use in pediatric subjects. Pediatric subjects are typically less than about 3 years old, or less than about 2 years old, or less than about 1 years old. Pediatric antigens can be administered multiple times over the course of 6 months, 1, 2 or 3 years. Pediatric antigens may be derived from a virus which may target pediatric populations and/or a virus from which pediatric populations are susceptible to infection. Pediatric viral antigens include antigens derived from one or more of Orthomyxovirus (influenza), Pneumovirus (RSV), Paramyxovirus (PIV and Mumps), Morbillivirus (measles), Togavirus (Rubella), Enterovirus (polio), HBV, Coronavirus (SARS), and Varicella-zoster virus (VZV), Epstein Barr virus (EBV). Pediatric bacterial antigens include antigens derived from one or more of *Streptococcus pneumoniae, Neisseria meningitides, Streptococcus pyogenes* (Group A *Streptococcus*), *Moraxella catarrhalis, Bordetella pertussis, Staphylococcus aureus, Clostridium tetani* (Tetanus), *Cornynebacterium diphtheriae*(Diphtheria), *Haemophilus influenzae* B (Hib), *Pseudomonas aeruginosa, Streptococcus agalactiae* (Group B *Streptococcus*), and *E. coli*. Examples of specific antigens derived from these pathogens are described above.

g. Antigens suitable for use in Elderly or Immunocompromised Individuals

The compositions of the invention can include one or more antigens suitable for use in elderly or immunocompromised individuals. Such individuals may need to be vaccinated more frequently, with higher doses or with adjuvanted formulations to improve their immune response to the targeted antigens. Antigens which may be targeted for use in elderly or immunocompromised individuals include antigens derived from one or more of the following pathogens: *Neisseria meningitides, Streptococcus pneumoniae, Streptococcus pyogenes* (Group A *Streptococcus*), *Moraxella catarrhalis, Bordetella pertussis, Staphylococcus aureus, Staphylococcus epidermis, Clostridium tetani* (Tetanus), *Cornynebacterium diphtheriae* (Diphtheria), *Haemophilus influenzae* B (Hib), *Pseudomonas aeruginosa, Legionella pneumophila, Streptococcus agalactiae* (Group B *Streptococcus*), *Enterococcus faecalis, Helicobacter pylori, Clamydia pneumoniae*, Orthomyxovirus (influenza), Pneumovirus (RSV), Paramyxovirus (PIV and Mumps), Morbillivirus (measles), Togavirus (Rubella), Enterovirus (polio), HBV, Coronavirus (SARS), Varicella-zoster virus (VZV), Epstein Barr virus (EBV), Cytomegalovirus (CMV). Examples of specific antigens derived from these pathogens are described above.

h. Antigens Suitable for use in Adolescent Vaccines

The compositions of the invention can include one or more antigens suitable for use in adolescent subjects. Adolescents may be in need of a boost of a previously administered pediatric antigen. Pediatric antigens which may be suitable for use in adolescents are described above. In addition, adolescents may be targeted to receive antigens derived from an STD pathogen in order to ensure protective or therapeutic immunity before the beginning of sexual activity. STD antigens which may be suitable for use in adolescents are described above.

i. Tumor Antigens

The compositions of the invention can include one or more tumor or cancer antigens. Tumor antigens can be, for example, peptide-containing tumor antigens, such as a polypeptide tumor antigen or glycoprotein tumor antigens. A tumor antigen can also be, for example, a saccharide-containing tumor antigen, such as a glycolipid tumor antigen or a ganglioside tumor antigen. A tumor antigen can further be, for example, a polynucleotide-containing tumor antigen that expresses a polypeptide-containing tumor antigen, for instance, an RNA vector construct or a DNA vector construct, such as plasmid DNA.

Tumor antigens include (a) polypeptide-containing tumor antigens, including polypeptides (which can range, for example, from 8-20 amino acids in length, although lengths outside this range are also common), lipopolypeptides and glycoproteins, (b) saccharide-containing tumor antigens, including poly-saccharides, mucins, gangliosides, glycolipids and glycoproteins, and (c) polynucleotides that express antigenic polypeptides.

Tumor antigens can be, for example, (a) full length molecules associated with cancer cells, (b) homologs and modified forms of the same, including molecules with deleted, added and/or substituted portions, and (c) fragments of the same. Tumor antigens can be provided in recombinant form. Tumor antigens include, for example, class I-restricted antigens recognized by CD8+ lymphocytes or class II-restricted antigens recognized by CD4+ lymphocytes.

Numerous tumor antigens are known in the art, including: (a) cancer-testis antigens such as NY-ESO-1, SSX2, SCP1 as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors), (b) mutated antigens, for example, p53 (associated with various solid tumors, e.g., colorectal, lung, head and neck cancer), p21/Ras (associated with, e.g., melanoma, pancreatic cancer and colorectal cancer), CDK4 (associated with, e.g., melanoma), MUM1 (associated with, e.g., melanoma), caspase-8 (associated with, e.g., head and neck cancer), CIA 0205 (associated with, e.g., bladder cancer), HLA-A2-R1701, beta catenin (associated with, e.g., melanoma), TCR (associated with, e.g., T-cell non-Hodgkins lymphoma), BCR-abl (associated with, e.g., chronic myelogenous leukemia), triosephosphate isomerase, KIA 0205, CDC-27, and LDLR-FUT, (c) over-expressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT 1 (associated with, e.g., various leukemias), carbonic anhydrase (associated with, e.g., renal cancer), aldolase A (associated with, e.g., lung cancer), PRAME (associated with, e.g., melanoma), HER-2/neu (associated with, e.g., breast, colon, lung and ovarian cancer), alpha-fetoprotein (associated with, e.g., hepatoma), KSA (associated with, e.g., colorectal cancer), gastrin (associated with, e.g., pancreatic and gastric cancer), telomerase catalytic protein, MUC-1 (associated with, e.g., breast and ovarian cancer), G-250 (associated with, e.g., renal cell carcinoma), p53 (associated with, e.g., breast, colon cancer), and carcinoembryonic antigen (associated with, e.g., breast cancer, lung cancer, and cancers of the gastrointestinal tract such as colorectal cancer), (d) shared antigens, for example, melanoma-melanocyte differentiation antigens such as MART-1/Melan A, gp100, MC1R, melanocyte-stimulating hormone receptor, tyrosinase, tyrosinase related protein-1/TRP1 and tyrosinase related protein-2/TRP2 (associated with, e.g., melanoma), (e) prostate associated antigens such as PAP, PSA, PSMA, PSH-P1, PSM-P1, PSM-P2, associated with e.g., prostate cancer, (f) immunoglobulin idiotypes (associated with myeloma and B cell lymphomas, for example), and (g) other tumor antigens, such as polypeptide- and saccharide-containing antigens including (i) glycoproteins such as sialyl Tn and sialyl Le$^x$ (associated with, e.g., breast and colorectal cancer) as well as various mucins; glycoproteins may be coupled to a carrier protein (e.g., MUC-1 may be coupled to KLH); (ii) lipopolypeptides (e.g., MUC-1 linked to a lipid moiety); (iii) polysaccharides (e.g., Globo H synthetic hexasaccharide), which may be coupled to a carrier proteins (e.g., to KLH), (iv) gangliosides such as GM2, GM12, GD2, GD3 (associated with, e.g., brain, lung cancer, melanoma), which also may be coupled to carrier proteins (e.g., KLH).

Other tumor antigens include p15, Hom/Mel-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, p185erbB2, p180erbB-3, c-met, mn-23H1, TAG-72-4, CA 19-9, CA 72-4, CAM 17.1, NuMa, K-ras, p16, TAGE, PSCA, CT7, 43-9F, 5T4, 791 Tgp72, beta-HCG, BCA225, BTAA, CA 125, CA 15-3 (CA 27.29\BCAA), CA 195, CA 242, CA-50, CAM43, CD68\KP1, CO-029, FGF-5, Ga733 (Ep-CAM), HTgp-175, M344, MA-50, MG7-Ag, MOV18, NB/70K, NY-CO-1, RCAS1, SDCCAG16, TA-90 (Mac-2 binding protein\cyclophilin C-associated protein), TAAL6, TAG72, TLP, TPS, and the like. These as well as other cellular components are described for example in United States Patent Publication No. 2002/0007173 and references cited therein.

Polynucleotide-containing antigens in accordance with the present invention typically comprise polynucleotides that encode polypeptide cancer antigens such as those listed above. Preferred polynucleotide-containing antigens include DNA or RNA vector constructs, such as plasmid vectors (e.g., pCMV), which are capable of expressing polypeptide cancer antigens in vivo.

Tumor antigens may be derived, for example, from mutated or altered cellular components. After alteration, the cellular components no longer perform their regulatory functions, and hence the cell may experience uncontrolled growth. Representative examples of altered cellular components include ras, p53, Rb, altered protein encoded by the Wilms' tumor gene, ubiquitin, mucin, protein encoded by the DCC, APC, and MCC genes, as well as receptors or receptor-like structures such as neu, thyroid hormone receptor, platelet derived growth factor (PDGF) receptor, insulin receptor, epidermal growth factor (EGF) receptor, and the colony stimulating factor (CSF) receptor. These as well as other cellular components are described for example in U.S. Pat. No. 5,693, 522 and references cited therein.

Bacterial and viral antigens, may be used in conjunction with the compositions of the present invention for the treatment of cancer. In particular, carrier proteins, such as CRM$_{197}$, tetanus toxoid, or *Salmonella typhimurium* antigen may be used in conjunction/conjugation with compounds of the present invention for treatment of cancer. The cancer antigen combination therapies will show increased efficacy and bioavailability as compared with existing therapies.

Additional information on cancer or tumor antigens can be found, for example, in Moingeon (2001) *Vaccine* 19:1305-1326; Rosenberg (2001) *Nature* 411:380-384; Dermine et al. (2002) *Brit. Med. Bull.* 62:149-162; Espinoza-Delgado (2002) *The Oncologist* 7(suppl 3):20-33; Davis et al. (2003) *J. Leukocyte Biol.* 23:3-29; Van den Eynde et al. (1995) *Curr. Opin. Immunol.* 7:674-681; Rosenberg (1997) *Immunol. Today* 18:175-182; Offringa et al. (2000) *Curr. Opin. Immunol.* 2:576-582; Rosenberg (1999) *Immunity* 10:281-287; Sahin et al. (1997) *Curr. Opin. Immunol.* 9:709-716; Old et al. (1998) *J. Exp. Med.* 187:1163-1167; Chaux et al. (1999) *J. Exp. Med.* 189:767-778; Gold et al. (1965) *J. Exp. Med.* 122:467-468; Livingston et al. (1997) *Cancer Immunol. Immunother.* 45:1-6; Livingston et al. (1997) *Cancer Immunol. Immunother.* 45:10-19; Taylor-Papadimitriou (1997) *Immunol. Today* 18:105-107; Zhao et al. (1995) *J. Exp. Med.* 182:67-74; Theobald et al. (1995) *Proc. Natl. Acad. Sci. USA* 92:11993-11997; Gaudernack (1996) *Immunotechnology* 2:3-9; WO 91/02062; U.S. Pat. No. 6,015,567; WO 01/08636; WO 96/30514; U.S. Pat. No. 5,846,538; and U.S. Pat. No. 5,869,445.

Further antigens may also include an outer membrane vesicle (OMV) preparation.

Additional formulation methods and antigens (especially tumor antigens) are provided in U.S. Patent Publication No. 2004/0202680. See also U.S. Pat. No. 6,884,435.

j. Antigen References

The compositions of the invention can include antigens described in any of the following references:

1 International Publication No. WO99/24578.
2 International Publication No. WO99/36544.
3 International Publication No. WO99/57280.
4 International Publication No. WO00/22430.
5 Tettelin et al. (2000) *Science* 287:1809-1815.
6 International Publication No. WO96/29412.
7 Pizza et al. (2000) *Science* 287:1816-1820.
8 International Publication No. WO 01/52885.
9 Bjune et al. (1991) *Lancet* 338(8775):1093-1096.
10 Fuskasawa et al. (1999) *Vaccine* 17:2951-2958.
11 Rosenqist et al. (1998) *Dev. Biol. Strand* 92:323-333.
12 Constantino et al. (1992) *Vaccine* 10:691-698.
13 Constantino et al. (1999) *Vaccine* 17:1251-1263.
14 Watson (2000) *Pediatr. Infect. Dis. J.* 19:331-332.
15 Rubin (2000) *Pediatr. Clin. North Am.* 47:269-285.
16 Jedrzejas (2001) *Microbiol. Mol. Biol. Rev.* 65:187-207.
17 International Publication No. WO 02/02606.
18 Kalman et al. (1999) *Nature Genetics* 21:385-389.
19 Read et al. (2000) *Nucleic Acids Res.* 28:1397-1406.
20 Shirai et al. (2000) *J. Infect. Dis.* 181(Suppl 3):S524-S527.
21 International Publication No. WO99/27105.
22 International Publication No. WO00/27994.
23 International Publication No. WO00/37494.
24 International Publication No. WO99/28475.
25 Bell (2000) *Pediatr. Infect. Dis. J.* 19:1187-1188.
26 Iwarson (1995) *APMIS* 103:321-326.
27 Gerlich et al. (1990) *Vaccine* 8 Suppl:S63-S68, S79-S80.
28 Hsu et al. (1999) *Clin. Liver Dis.* 3:901-915.
29 Gastofsson et al. (1996) *N. Engl. J. Med.* 334:349-355.
30 Rappuoli et al. (1991) *TIBTECH* 9:232-238.
31 Plotkin, S. A. et al., *Vaccines*, 4$^{th}$ ed., W.B. Saunders Co. (2004)
32 Del Guidice et al. (1998) *Mol. Aspects Med.* 19:1-70.
33 International Publication No. WO93/018150.
34 International Publication No. WO99/53310.
35 International Publication No. WO98/04702.
36 Ross et al. (2001) *Vaccine* 19:135-142.
37 Sutter et al. (2000) *Pediatr. Clin. North Am.* 47:287-308.
38 Zimmerman & Spann (1999) *Am. Fam. Physician* 59:113-118, 125-126.
39 Dreensen (1997) *Vaccine* 15 Suppl:S2-S6.
40 *MMWR Morb. Mortal Wkly Rep.* (1998) 16:47(1):12, 19.
41 McMichael (2000) *Vaccine* 19 Suppl 1:S101-S107.
42 Schuchat (1999) *Lancet* 353(9146):51-56.
43 GB patent applications 0026333.5, 0028727.6 & 0105640.7.
44 Dale (1999) *Infect. Disclin. North Am.* 13:227-243.
45 Ferretti et al. (2001) *Proc. Natl. Acad. Sci. USA* 98:4658-4663.
46 Kuroda et al. (2001) *Lancet* 357(9264):1225-1240.
47 Ala'Aldeen et al. (2001) *Lancet* 357(9264):1218-1219.
48 Ramsay et al. (2001) *Lancet* 357(9251):195-196.
49 Lindberg (1999) *Vaccine* 17 Suppl 2:S28-S36.
50 Buttery & Moxon (2000) *J. R. Coil Physicians Long* 34:163-168.
51 Ahmad & Chapnick (1999) *Infect. Dis. Clin. North Am.* 13:113-133.
52 Goldblatt (1998) *J. Med. Microbiol.* 47:663-667.
53 European Patent No. EP 0 477 508B1.
54 U.S. Pat. No. 5,306,492.
55 International Publication No. WO98/42721.
56 Cruse et al. (eds.) *Conjugate Vaccines*, particularly vol. 10:48-114.
57 Hermanson, G. T., *Bioconjugate Techniques*, 1st ed., Academic Press (1996).
58 European Patent Publication No. 0 372 501.
59 European Patent Publication No. 0 378 881.
60 European Patent Publication No. 0 427 347.
61 International Publication No. WO 93/17712.
62 International Publication No. WO 98/58668.
63 European Patent Publication No. 0 471 177.
64 International Publication No. WO00/56360.
65 International Publication No. WO 00/67161.

The contents of all of the above cited patents, patent applications and journal articles are incorporated by reference as if set forth fully herein.

4. Further Pharmaceuticals

In addition to immunogenic species such as those above (e.g., immunological adjuvants and antigens), a near limitless variety of further pharmaceuticals may be used. Examples of such pharmaceuticals include the following, among many others: antibiotics and antiviral agents, nonsteroidal antiinflammatory drugs, analgesics, vasodilators, cardiovascular drugs, psychotropics, neuroleptics, antidepressants, antiparkinson drugs, beta blockers, calcium channel blockers, bradykinin inhibitors, ACE-inhibitors, vasodilators, prolactin inhibitors, steroids, hormone antagonists, antihistamines, serotonin antagonists, heparin, chemotherapeutic agents, antineoplastics and growth factors, including but not limited to PDGF, EGF, KGF, IGF-1 and IGF-2, FGF, hormones including peptide hormones such as insulin, proinsulin, growth hormone, GHRH, LHRH, EGF, somatostatin, SNX-111, BNP, insulinotropin, ANP, FSH, LH, PSH and hCG, gonadal steroid hormones (androgens, estrogens and progesterone), thyroid-stimulating hormone, inhibin, cholecystokinin, ACTH, CRF, dynorphins, endorphins, endothelin, fibronectin fragments, galanin, gastrin, insulinotropin, glucagon, GTP-binding protein fragments, guanylin, the leukokinins, magainin, mastoparans, dermaseptin, systemin, neuromedins, neurotensin, pancreastatin, pancreatic polypeptide, substance P, secretin, thymosin, and the like, enzymes, transcription or translation mediators, intermediates in metabolic pathways, and immunomodulators, such as any of the various cytokines including interleukin-1, interleukin-2, interleukin-3, interleukin-4, and gamma-interferon.

5. Surfactants and/or Cryoprotective Agents

As noted above, one or more surfactants and/or one or more cryoprotective agents may be optionally added to the compositions of the invention, for example, to ensure that lyophilized nanoparticles can be resuspended without an unacceptable increase in size (e.g., without significant aggregation).

Surfactants include cationic, anionic, zwitterionic, and nonionic surfactants. Cationic surfactants include, for example, cetyltrimethylammonium bromide or "CTAB" (e.g., cetrimide), benzalkonium chloride, DDA (dimethyl dioctodecyl ammonium bromide), and DOTAP (dioleoyl-3-trimethylammonium-propane), among others. Anionic surfactants include, for example, SDS (sodium dodecyl sulfate), SLS (sodium lauryl sulfate), DSS (disulfosuccinate), and sulphated fatty alcohols, among others. Nonionic surfactants include, for example, PVA (polyvinyl alcohol), povidone (also known as polyvinylpyrrolidone or PVP), sorbitan esters, polysorbates, polyoxyethylated glycol monoethers, polyoxyethylated alkyl phenols, and poloxamers, among others.

In some embodiments, one or more surfactants is/are added to the compositions of the invention in an amount effective to promote nanoparticle suspension (and resuspension after lyophilization). The weight ratio of the surfactant to the biodegradable polymer may range, for example, from less than 0.001:1 to 0.5:1 or more, for example, ranging from 0.005:1 to 0.1:1, among other ratios. In general ionic surfactants are used in lower ratios than nonionic surfactants.

Common cryoprotective agents include (a) amino acids such as glutamic acid and arginine, among others; (b) polyols, including diols such as ethylene glycol, propanediols such as 1,2-propylene glycol and 1,3-propylene glycol, and butane diols such as 2,3-butylene glycol, among others, triols such as glycerol, among others, as well as other higher polyols; and (c) carbohydrates including, for example, (i) monosaccharides (e.g., glucose, galactose, and fructose, among others), (ii) polysaccharides including disaccharides (e.g., sucrose, lactose, trehalose, maltose, gentiobiose and cellobiose, among others), trisaccharides (e.g., raffinose, among others), tetrasaccharides (e.g., stachyose among others), pentasaccharides (e.g., verbascose among others), as well as numerous other higher polysaccharides, and (iii) alditols such as xylitol, sorbitol, and mannitol, among others (in this regard, is noted that alditols are higher polyols, as well as being carbohydrates).

In some embodiments, one or more cryoprotective agents is/are added to the compositions of the invention in an amount effective to promote nanoparticle suspension (and resuspension after lyophilization). The weight ratio of the cryoprotecitve agent to the biodegradable polymer may range, for example, from less than 0.01:1 to 0.5:1 or more, for example, ranging from 0.05:1 to 0.1:1, among other ratios.

6. Supplemental Components

The pharmaceutical compositions of the present invention may optionally include one or more of a wide variety of supplemental components including one or more pharmaceutically acceptable excipients. For example, vehicles such as water, saline, glycerol, polyethylene glycol, ethanol, etc. may be used. Other excipients, such as wetting or emulsifying agents, tonicity adjusting agents, biological buffering substances, and the like, may be present. A biological buffer can be virtually any species which is/are pharmacologically acceptable and which provide the formulation with the desired pH, i.e., a pH in the physiological range. Examples of buffered systems include phosphate buffered saline, Tris buffered saline, Hank's buffered saline, and the like. Other buffer systems include those set forth above for use in the nanoparticle formation process.

Depending on the final dosage form, other excipients known in the art can also be introduced, including binders, disintegrants, fillers (diluents), lubricants, glidants (flow enhancers), compression aids, sweeteners, flavors, preservatives, suspending/dispersing agents, film formers/coatings, and so forth.

7. Administration

Nanoparticle compositions in accordance with the invention can be administered parenterally, e.g., by injection (which may be needleless). The compositions can be injected subcutaneously, intradermally, intramuscularly, intravenously, intraarterially, or intraperitoneally, for example. Other modes of administration include nasal, mucosal, intraoccular, rectal, vaginal, oral and pulmonary administration, and transdermal or transcutaneous applications.

In some embodiments, the compositions of the present invention can be used for site-specific targeted delivery. For example, intravenous administration of the compositions can be used for targeting the lung, liver, spleen, blood circulation, or bone marrow.

Treatment may be conducted according to a single dose schedule or a multiple dose schedule. A multiple dose schedule is one in which a primary course of administration may be given, for example, with 1-10 separate doses, followed by other doses given at subsequent time intervals, chosen to maintain and/or reinforce the therapeutic response, for example at 1-4 months for a second dose, and if needed, a subsequent dose(s) after several months. The dosage regimen will also be, at least in part, determined by the need of the subject and be dependent on the judgment of the practitioner.

Furthermore, if prevention of disease is desired, the compositions are generally administered prior to the arrival of the primary occurrence of the infection or disorder of interest. If other forms of treatment are desired, e.g., the reduction or elimination of symptoms or recurrences, the compositions are generally administered subsequent to the arrival of the primary occurrence of the infection or disorder of interest.

C. EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Materials.

Polylactide-co-glycolide(PLG), RG502H with a copolymer ratio of 50:50 was obtained from Boehringer Ingleheim (Ingelheim, Germany). Sucrose and mannitol for lyophilization were obtained from Sigma Chemicals (St Louis, Mo.). Polyvinyl alcohol (PVA) (MW=15000) was obtained from ICN Biomedicals (now MP Biomedicals, Irvine, Calif.). Acetone was obtained from EMD Chemicals (Gibbstown, N.J.). *Escherichia Coli*-derived recombinant meningococcal vaccine candidate MB1 from Novartis Vaccines was isolated and purified as described here. M. Comanducci, et al., "NadA, a Novel Vaccine Candidate of Neisseria meningitides," *J. Exp. Med.* 195:1445-1454 (2002). Tris-EDTA buffer was obtained from Novartis Vaccines. SMIP (Imidazoquinoline 090) synthesis is described in Int. Pub. Nos. WO 2006/031878 to Valiante et al. and WO 2007/109810 to Sutton et al.

Example 1

Preparation of Nanoparticles

Poly(lactide-co-glycolide) nanoparticles were prepared based on the solvent displacement method. An organic phase with PLG dissolved in acetone was added dropwise to Tris EDTA buffer placed on a gyrotory shaker-model G2 (New Brunswick Scientific Co, Inc., N.J., USA) at 120 rpm and the acetone was allowed to evaporate overnight. The SMIP was encapsulated by co-dissolving it with PLG in the organic phase. Sizes of the particles prepared depended on the PLG concentration as seen below. There was no surfactant present in either the aqueous phase or the organic phase.

The size distribution of the particles [D(v,0.5)] was determined with a Zetasizer 3000HsA (Malvern, Worcestershire, UK), at a scattering angle of 90° at 25° C. Each nanoparticle preparation was analyzed with 10 readings per sample after dilution of nanoparticles in water. The measurements were run in triplicates. This instrument measures the size of the particles based on dynamic light scattering. The particles were considered as nanoparticles if there were no aggregates and a single monodisperse peak was obtained. The zeta potential was measured with the Zetasizer with a typical diluted concentration of 0.2 mg/ml PLG in water.

The different sized nanoparticles (see Table 1 below) were formulated by adjusting the initial PLG concentration in the organic phase. Small particles (~130 nm) were prepared with 10 ml of 0.05% (w/v) PLG in acetone added drop-wise to 10 ml of water. Intermediate sized particles (~180 nm) were made with 10 ml of 2% (w/v) PLG in acetone added to 10 ml of water. Large particles (~240 nm) were prepared with 10 ml of 3.0% PLG (w/v) in acetone added to 10 ml of water. The zeta potential for the particles was ~45 mV.

TABLE 1

Particle Size vs. PLG concentration.

| PLG Concentration | Particle size |
|---|---|
| RG 502H 0.5% w/v (5 mg/ml) | 130 nm |
| RG 502H 1% w/v (10 mg/ml) | 160 nm |
| RG 502H 2% w/v (20 mg/ml) | 180 nm |
| RG 502H 2.5% w/v (25 mg/ml) | 225 nm |
| RG 502H 3% w/v (30 mg/ml) | 240 nm |

Since the nanoparticle formation process does not use any surfactant, a known volume of the nanoparticle suspension was freeze-dried and the PLG content was determined. More specifically, the PLG content of the suspension was determined by aliquoting a 1 ml volume into four pre-weighed vials, which were lyophilized and weighed again with the average net weight used as the PLG content. The PLG recovery was found to be consistently greater than 90% for polymer concentrations ranging from 10 mg/ml to 25 mg/ml. With concentrations higher than 25 mg/ml, the particle size was greater than 225 nm and these concentrations were not investigated further.

Initially, the nanoparticle suspension was agitated with a magnetic stirrer. However, this caused polymer to aggregate forming clumps, resulting in lower recovery for the nanoparticles. This issue was successfully addressed by placing the nanoparticle suspension on a gyrotory shaker, which prevented aggregation of particles.

Example 2

SMIP Encapsulation

All the particles that were used for the encapsulation of SMIP were formed using RG 502H 2% w/v (20 mg/ml) with SMIP concentrations of 1% and 2% w/w relative to the polymer.

Nanoparticles with a theoretical SMIP loading level of 2% w/w of PLG were prepared for the SMIP encapsulation study. Both water (pH 5.5-6) and Tris EDTA buffer (pH 7-8) were used for the aqueous phases. The aqueous phase pH influences the ionization of a given adjuvant and hence its solubility. Since, a basic SMIP is being employed here, Tris EDTA buffer was used for the aqueous phase, which maintained the pH of the suspension between 7 and 8.

The encapsulation efficiency was calculated as a ratio of mass of SMIP in the nanoparticles to the mass of SMIP used in the formulation. More particularly, the nanoparticle suspension was aliquoted (1 ml) into 2 vials and centrifuged at 16000 RPM for 30 minutes. The amount of SMIP in the supernatant was determined using an ultra performance liquid chromatography (Waters Acquity UPLC, Milford, Mass., USA) assay. The pellet was washed three times and the amount of SMIP in the pellet was determined after hydrolyzing the pellet with sodium hydroxide, followed by neutralization with hydrochloric acid. Encapsulation efficiency was calculated as ratio of the SMIP in the pellet to the total SMIP content of the suspension. Mass balance was achieved by hydrolyzing 1 ml of the suspension and determining the total SMIP content in 1 ml of the suspension.

The encapsulation efficiency ranged from 40-50% when water was used in the aqueous phase whereas with Tris EDTA buffer as the aqueous phase, the encapsulation efficiency was greater than 90%. The increased encapsulation efficiency is most likely due to a change in the degree of ionization. Without wishing to be bound by theory, it is hypothesized that, because a SMIP in base form was employed, increasing the pH may have reduced its migration into the aqueous phase, enhancing SMIP encapsulation in the nanoparticle.

Example 3

Protein Adsorption

MenB protein was adsorbed to the SMIP-encapsulated particles of Example 2 by incubating them in a Tris EDTA buffer (and no other excipients) overnight on a lab rocker at 4° C. After protein adsorption, additional surfactant and sugar excipients (10% PVA w/w of polymer as well as 4% Sucrose and 3% Mannitol w/v of reconstitution) were added before lyophilization. An advantage to nanoparticles in comparison with microparticles is the greater available surface area that facilitates increased protein loading levels. The increased protein loading level allows for delivery of the same amount of protein antigen with less PLG and less amount of surfactant used in lyophilization.

Excipients were added to the nanoparticle suspensions immediately prior to lyophilization. The suspensions were placed in glass vials and frozen at −80° C. for 30 minutes.

Lyophilization was carried out in a Labconce Freeze Dry System, Freezone 4.5 (Kansas City, Mo.) operating at −49° C. and vacuum less than 133×10$^{-3}$ mBar for approximately 24 h. All samples were reconstituted with 1 ml sterile water for injection.

The reconstituted samples were centrifuged, and the supernatant was separated from the pellet. The amount of protein in the supernatant was measured by high-performance liquid chromatography (HPLC) with a gel-permeation column with ultraviolet (UV) detection at 214 nm, and was semi-quantitatively confirmed by the SDS-PAGE gels. The detection limit of the UV detector is 1 µg/ml. This leads to a typical error of less than 5% for the amount of protein adsorbed. The results from the size exclusion chromatography assay indicated that there was no protein-antigen present in the supernatant, which implies that the protein was at least 95% associated with the particles (allowing for 5% error).

The formulation was also characterized for size distribution, pH, osmolarity and endotoxin content post-lyophilization after reconstituting in 1 ml of sterile water. The size distribution was determined with Zetasizer 3000HsA (Malvern, Worcestershire, UK), and the results are presented in Table 2.

TABLE 2

| | | |
|---|---|---|
| RG 502H nanoparticles/2% SMIP (w/w)/protein-antigen adsorbed on surface | 177 nm | 196.5 nm |
| RG 502H nanoparticles/1% SMIP (w/w)/protein antigen adsorbed on surface | 182 nm | 202.5 nm |

The pH was measured using pH-indicator strips (colorpHast, EMD Chemicals, Gibbstown, N.J.). The pH of the nanoparticle suspension post-lyophilization was found to be around 5.5.

The osmolarity of the formulation was determined using a vapor pressure osmometer (Wescor Inc., Logan, Utah). The osmolarity of the formulations were in the range of 260-320 mOsm/L.

The endotoxin content of the formulation was determined by placing the appropriately diluted PLG nanoparticle formulation in an Endosafe PTS system (Charles River Laboratories, Wilmington, Mass., USA). This is an FDA-licensed endotoxin detection system that utilizes an LAL test cartridge to determine the endotoxin levels in the sample and has a sensitivity of 0.01-1.0 EU/ml. The endotoxin levels as determined by the Endosafe PTS system were less than 1.43 EU/ml.

Example 4

In Vitro Release of SMIP

In vitro release studies for lyophilized and non-lyophilized formulations with adsorbed protein were compared using nanosuspensions (1 ml) having SMIP concentrations of 1% and 2% w/w relative to the polymer. The polymer concentrations used to form the nanoparticles were maintained at 2% w/v. In vitro release profiles were measured by determining the SMIP content in the supernatant of the nanosuspensions (volume 1 ml). The formulations were reconstituted in sterile water to give a total SMIP concentration of 120 ug/ml. The suspensions were kept stirring at 37° C. The suspensions were periodically centrifuged and the supernatant was analyzed using an ultra performance liquid chromatography assay to determine the amount of SMIP in the supernatant.

Figure 2:
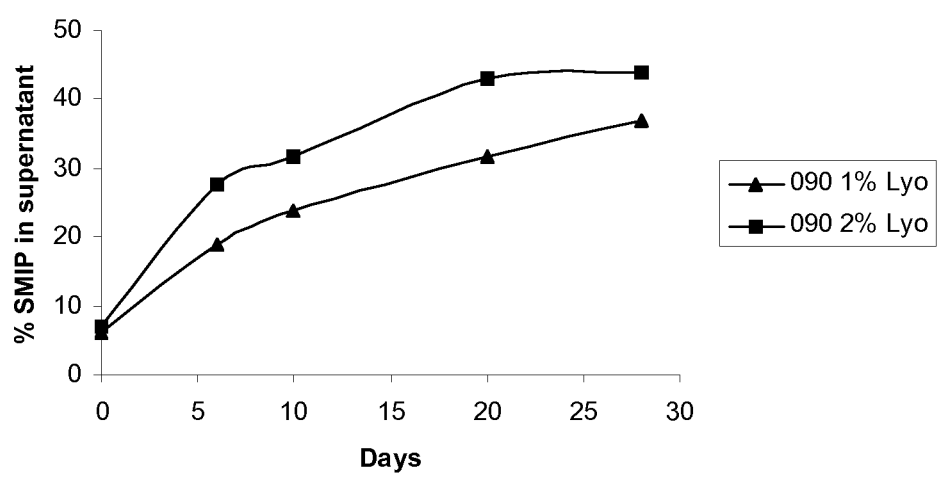
FIG. 2 is a plot of the in vitro release profile of a lyophilized suspension at a SMIP concentration 1% and 2% w/w relative to the polymer.

As seen from FIG. 1, the non-lyophilized suspensions released the SMIP content completely in two weeks. As seen from FIG. 2, on the other hand, the lyophilized formulations released only about 40% of the total SMIP content in 2 weeks. Without wishing to be bound by theory, it was hypothesized that this could be due to the interaction of the PVA with the PLGA, such that the PVA forms a protective layer around PLGA.

Although preferred embodiments of the subject invention have been described in some detail, it is understood that obvious variations can be made without departing from the spirit and the scope of the invention.

The invention claimed is:

1. A method of forming nanoparticles comprising:
   contacting a first liquid that comprises a biodegradable polymer dissolved in an organic solvent with a second liquid that comprises an aqueous solvent by minimally intermixing the first and second liquid such that (i) nanoparticles are formed without particle aggregation without detergent; (ii) the polymeric yield for the nanoparticles is >90% and (iii) the D(v,0.5) value for the nanoparticles is less than 200 wherein the second liquid is miscible with the organic solvent while being a non-solvent for the biodegradable polymer.

2. The method of claim 1, wherein the biodegradable polymer is a poly(alpha-hydroxy acid).

3. The method of claim 1, wherein the biodegradable polymer is selected from polymers comprising polylactide, polyglycolide or poly(lactide-co-glycolide).

4. The method of claim 1, wherein the biodegradable polymer concentration in the first liquid ranges from 0.5 to 3% w/v.

5. The method of claim 1, wherein the shaking is performed using a gyrotory shaker.

6. The method of claim 1, wherein the first liquid is added to the second liquid in a dropwise fashion.

7. The method of claim 1, further comprising allowing the organic solvent to evaporate.

8. The method of claim 1, wherein the organic solvent is a hydrophilic organic solvent.

9. The method of claim 1, wherein the organic solvent is acetone.

10. The method of claim 1, wherein the first liquid further comprises a pharmaceutical.

11. The method of claim 10, wherein the pharmaceutical is an immunogenic species.

12. The method of claim 11, wherein the immunogenic species is an antigen.

13. The method of claim 11, wherein the immunogenic species stimulates an innate immune response.

14. The method of claim 11, wherein the immunogenic species selected from immunostimulatory oligonucleotides, imidazoquinoline compounds, loxoribine, bropirimine, bacterial lipopolysaccharides, peptidoglycan, bacterial lipoproteins, bacterial flagellins, single-stranded RNA, double-stranded RNA, saponins, lipotechoic acid, ADP-ribosylating toxins and detoxified derivatives thereof, polyphosphazene, muramyl peptides, thiosemicarbazone compounds, tryptanthrin compounds, and lipid A derivatives.

15. The method of claim 11, wherein the immunogenic species is an activator of a Toll-like receptor (TLR).

16. The method of claim 11, wherein the immunogenic species is an activator of a Toll-like receptor (TLR) selected from Toll-like receptor 7 (TLR 7), Toll-like receptor 8 (TLR8), or a combination thereof.

17. The method of claim 11, wherein the immunogenic species is an imidazoquinoline compound.

18. The method of claim 11, wherein the immunogenic species is selected from resimiquod, imiquimod, imidazoquinoline 090, and combinations thereof.

19. The method of claim 11, wherein said method has an encapsulation efficiency for said immunogenic species of 50% or more.

20. The method of claim 11, wherein the amount of immunogenic species relative to the biodegradable polymer used in the method ranges from 0.5 to 2%.

21. A method of forming nanoparticles comprising: contacting a first liquid that comprises a biodegradable polymer dissolved in an organic solvent with a second liquid that comprises an aqueous solvent comprising a buffer by minimally intermixing the first and second liquid such that (i) nanoparticles are formed without particle aggregation with or without detergent; (ii) the polymeric yield for the nanoparticles is >90% and (iii) the D(v,0.5) value for the nanoparticles is less than 200 nm, wherein the second liquid is miscible with the organic solvent while being a non-solvent for the biodegradable polymer.

22. The method of claim 21, wherein the biodegradable polymer is a poly(alpha-hydroxy acid).

23. The method of claim 21, wherein the biodegradable polymer is selected from polymers comprising polylactide, polyglycolide or poly(lactide-co-glycolide).

24. The method of claim 21, wherein the biodegradable polymer concentration in the first liquid ranges from 0.5 to 3% w/v.

25. The method of claim 21, further comprising allowing the organic solvent to evaporate.

26. The method of claim 21, wherein the organic solvent is a hydrophilic organic solvent.

27. The method of claim 21, wherein the organic solvent is acetone.

28. The method of claim 21, wherein the first liquid further comprises a pharmaceutical.

29. The method of claim 28, wherein the pharmaceutical is an immunogenic species.

30. The method of claim 29, wherein the immunogenic species is an antigen.

31. The method of claim 29, wherein the immunogenic species stimulates an innate immune response.

32. The method of claim 29, wherein the immunogenic species is selected from immunostimulatory oligonucleotides, imidazoquinoline compounds, loxoribine, bropirimine, bacterial lipopolysaccharides, peptidoglycan, bacterial lipoproteins, bacterial flagellins, single-stranded RNA, double-stranded RNA, saponins, lipotechoic acid, ADPribosylating toxins and detoxified derivatives thereof, polyphosphazene, muramyl peptides, thiosemicarbazone compounds, tryptanthrin compounds, and lipid A derivatives.

33. The method of claim 29, wherein the immunogenic species is an activator of a Toll-like receptor (TLR).

34. The method of claim 29, wherein the immunogenic species is an activator of a Toll-like receptor (TLR) selected from Toll-like receptor 7 (TLR 7), Toll-like receptor 8 (TLR8), or a combination thereof.

35. The method of claim 29, wherein the immunogenic species is an imidazoquinoline compound.

36. The method of claim 29, wherein the immunogenic species is selected from resimiquod, imiquimod, imidazoquinoline 090, and combinations thereof.

37. The method of claim 29, wherein the immunogenic species is a proton-accepting immunogenic species and wherein the buffer is selected to maintain a pH that is greater than the pKa of the immunogenic species.

38. The method of claim 29, wherein the immunogenic species is an imidazoquinoline compound and wherein the buffer is selected to maintain a pH ranging from 7.5 to 8.5.

39. The method of claim 29, wherein the immunogenic species is a proton donating immunogenic species and wherein the buffer is selected to maintain a pH that is less than the pKa of the immunogenic species.

40. The method of claim 29, wherein said method has an encapsulation efficiency for said immunogenic species of 80% or more.

41. The method of claim 29, wherein the amount of immunogenic species relative to the biodegradable polymer used in the method ranges from 0.5 to 3%.

42. The method of claim 21, wherein the first and second liquids are contacted under conditions of gentle shaking.

43. The method of claim 21, wherein the first liquid is added to the second liquid in a dropwise fashion.

44. The method of claim 1, wherein minimally intermixing the first and second liquid comprises gradual introduction of the first liquid into the second liquid.

45. The method of claim 21, wherein minimally intermixing the first and second liquid comprises gradual introduction of the first liquid into the second liquid.

46. The method of claim 1, wherein minimally intermixing the first and second liquid comprises conditions of gentle shaking with no stirring.

47. The method of claim 21, wherein minimally intermixing the first and second liquid comprises conditions of gentle shaking with no stirring.

48. The method of claim 44, wherein the gradual introduction is by dropwise addition, careful pouring, or gentle injection of the first liquid into the second liquid.

49. The method of claim 45, wherein the gradual introduction is by dropwise addition, careful pouring, or gentle injection of the first liquid into the second liquid.

* * * * *